US011836215B2

United States Patent
Wismüller

(10) Patent No.: US 11,836,215 B2
(45) Date of Patent: Dec. 5, 2023

(54) METHOD AND DEVICE FOR DETERMINING A MEASURE OF CAUSAL INFLUENCE BETWEEN COMPONENTS OF COMPLEX SYSTEMS

(71) Applicant: Axel W. E. Wismüller, Rochester, NY (US)

(72) Inventor: Axel W. E. Wismüller, Rochester, NY (US)

( * ) Notice: Subject to any disclaimer, the term of this patent is extended or adjusted under 35 U.S.C. 154(b) by 111 days.

(21) Appl. No.: 17/413,273

(22) PCT Filed: May 6, 2020

(86) PCT No.: PCT/US2020/031617
§ 371 (c)(1),
(2) Date: Jun. 11, 2021

(87) PCT Pub. No.: WO2020/206466
PCT Pub. Date: Oct. 8, 2020

(65) Prior Publication Data
US 2022/0058211 A1    Feb. 24, 2022

Related U.S. Application Data

(60) Provisional application No. 62/814,953, filed on Mar. 7, 2019.

(51) Int. Cl.
*G06F 17/18*    (2006.01)
*G06F 16/2455*    (2019.01)
(Continued)

(52) U.S. Cl.
CPC .......... *G06F 17/18* (2013.01); *G06F 16/2264* (2019.01); *G06F 16/24558* (2019.01); *G06F 16/288* (2019.01)

(58) Field of Classification Search
CPC .. G06F 17/18; G06F 16/24558; G06F 16/288; G06F 16/2264
(Continued)

(56) References Cited

U.S. PATENT DOCUMENTS

| 7,409,321 B2 * | 8/2008 | Repucci | ................. G06Q 90/00 702/189 |
| 8,626,680 B2 * | 1/2014 | Lozano | ................... G06F 17/18 706/12 |

(Continued)

FOREIGN PATENT DOCUMENTS

WO    2020018675 A1    1/2020

OTHER PUBLICATIONS

Wismuller et al., "Large-scale Extended Granger Causality (IsXGC) for classification of Autism Spectrum Disorder from esting-state functional MRI", Progress in Biomedical Optics and Imaging, SPIE—International Ociety for Optical Engineering, Bellingham WA, USA, vol. 11314, pp. 113141Y-1-113141Y-8, 2020.*
(Continued)

*Primary Examiner* — Giovanna B Colan
(74) *Attorney, Agent, or Firm* — Hooker & Habib, P.C.

(57) ABSTRACT

Disclosed is a computer-implemented method for determining a measure of the causal interdependence of a source dataset S and a target dataset Y in the simultaneous presence of a non-empty confounding dataset B. The method includes a dimensional modification step to reduce the complexity of the data and an augmentation step to add information to the dimensionally modified data without a significant increase in size or complexity of the data. The augmented dimensionally modified data is used to calculate a measure of the causality or relatedness between the source dataset S and the target dataset Y. The method enables linear or nonlinear causality analysis of high-dimension multivariate time-se-
(Continued)

ries or features datasets, such as time-series datasets generated by functional MRI full-brain scans.

20 Claims, 10 Drawing Sheets

(51) Int. Cl.
  *G06F 16/28* (2019.01)
  *G06F 16/22* (2019.01)
(58) Field of Classification Search
  USPC .......................................................... 707/758
  See application file for complete search history.

(56) References Cited

U.S. PATENT DOCUMENTS

2019/0021594 A1* 1/2019 Sommerlade ........ A61B 5/7207
2019/0206057 A1* 7/2019 Cranmer ................. G06F 17/16

OTHER PUBLICATIONS

"Exploring connectivity with large-scale Granger causality on resting-state functional MRI," Adora M. Dsouza, Anas Z. Abidin, Lutz Leistritz, Axel Wismuller; Journal of Neuroscience Methods; Amsterdam, NL; Jun. 16, 2017.*
European Patent Office, International Search Report in corresponding PCT/IB2020/031617, dated Sep. 1, 2020, 12 pages.
Wismüller et al., "Large-scale Extended Granger Causality (lsXGC) for classification of Autism Spectrum Disorder from resting-state functional MRI", Progress in Biomedical Optics and Imaging, SPIE—International Society for Optical Engineering, Bellingham WA, USA, vol. 11314, pp. 113141Y-1-113141Y-8, Mar. 16, 2020.
DSouza et al., "Exploring connectivity with large-scale Granger causality on resting-state functional MRI", Journal of Neuroscience Methods, Amsterdam, NL, vol. 287, Jun. 16, 2017, pp. 68-79.
Guyon et al., "Causal Feature Selection", Computational Methods of Feature Selection, Oct. 29, 2007, pp. 63-85.
Wismüller et al., Pair-wise Clustering of Large Scale Granger Causality Index Matrices for Revealing Communities. Proc. of SPIE, Int. Soc. Opt. Eng. Mar. 13, 2014;9038: doi:10.1117/12.2044340 (2014).
Winkler et al., "Vailidy of time reversal for testing Granger causality", arXiv:1509.07636v2 [math.ST] Feb. 11, 2016.
Sugihara, R. May, H. Ye, C.H. Hsieh, E.R. Deyle, M. Fogarty, and S. Munch, "Detecting causality in complex ecosystems", Science 338:496-500, 2012.
Schreiber T:, "Measuring information transfer", Phys Rev Lett 85(2):461-464 (2000).
Palus et al., "Synchronization as adjustment of information rates: Detection from bivariate time series", Physical Review E, vol. 63, Mar. 28, 2001, pp. 046211-1-0426211-6 (six pages).
Ancona et al. "An Invariance Property of Predictors in Kernal-Induced Hypothesis Spaces", Neural Computation, vol. 18, pp. 749-759 (2006).
Marinazzo et al., "Nonlinear parametric model for Granger causality of time series", Physical Review E 73, Jun. 20, 2006, pp. 066216-1-066216-6 (six pages).
DSousa, "Directed Network Recovery from Large Systems with Applications in Functional Magnetic Resonance Imaging (fMRI)", PhD Thesis, University of Rochester College of Engineering, Rochester, New York, 181 pages (2019).

* cited by examiner

METHOD AND DEVICE FOR DETERMINING A MEASURE OF CAUSAL INFLUENCE BETWEEN COMPONENTS OF COMPLEX SYSTEMS

RELATED APPLICATION

This application claims priority to and the benefit of the filing date of my U.S. provisional patent application with appendices filed Mar. 7, 2019 at Ser. No. 62/814,953 titled "Method and Device for Determining a Measure of Causal Influence Between Components of Complex Systems" and, incorporated by reference as if fully set forth herein.

FIELD OF THE DISCLOSURE

This disclosure relates to methods and related devices for determining relationships between components of high-dimensional multivariate systems, and in particular, high-dimensional multivariate systems that are underdetermined.

BACKGROUND OF THE DISCLOSURE

High-dimensional multivariate systems include datasets D that can be arranged as having N rows of data, each row having T columns of data values, that is, $D \in \mathbb{R}^{N \times T}$, where $N \geq 3$. A multivariate dataset D may be a time-series dataset or may be a features dataset. A time-series dataset has columns of simultaneously measured values arranged in temporal order of measurement. A features dataset has rows made up of features, the columns multi-dimensional data samples or vectors whose elements represent the value of each feature for a given sample.

With respect to multivariate time-series, causal influence between two simultaneously recorded time-series may be evaluated using the concept of Granger causality. If a prediction error of one of the time series is reduced by use of information provided by the other time-series, then the other time-series is said to demonstrate a causal influence on the one time series, see [8].

Granger causality was first developed and applied to linear analysis of bivariate time-series. Extensions of Granger causality to non-linear analysis of bivariate time-series have since been developed. For example, [9] discloses an approach for non-linear Granger causality of a bivariate time-series using a radial basis function (RBF) network. A RBF is a real-valued function whose value depends only on the distance between the input and the fixed points. RBFs can be used to approximate other functions, so radial basis functions are used in machine learning algorithms to learn and approximate functional relationships. The fixed points can be established from training data by any clustering method, such as k-means clustering or any of its variants from prior art, or by using the training data itself, either directly or after any type of suitable pre-processing, as the fixed points.

The approach in [9] uses radial basis functions because Gaussian RBF functions are "IIV invariant". It has been shown in [10] that IIV invariance is a mathematically relevant property applicable to machine learning approaches used in evaluating non-linear causality between two simultaneously acquired time-series. The results for function approximators using models that are IIV invariant do not change when statistically independent variables are added as input variables and so can recognize pairs of time-series without a causal relationship.

However, applying Granger causality or some other causality measure to evaluate causality between pairs of time-series of high-dimensional multivariate time-series (an ensemble of time-series $X \in \mathbb{R}^{N \times T}$ where $N \geq 3$ is the number of time-series and T the number of temporal values) is problematical. High-dimensionality data is found in many fields, including econometrics, the neurosciences, the social sciences, social network operations, and others. High-dimensionality data renders many standard statistical techniques invalid or computationally expensive (the "curse of dimensionality"). Furthermore, many high-dimensional multivariate time-series X are underdetermined, that is, the time-series include a relatively low number of temporal values. The relatively low number T makes parameter optimization of non-linear time series models impossible or very challenging.

One application of high-dimensional multivariate time-series analysis is in the field of functional magnetic resonance imaging (fMRI) data analysis. FMRI measures variations of brain signals caused by neuronal activity. The MRI scanner detects changes in the magnetic properties of blood caused by the blood releasing oxygen to active neurons, the blood oxygenation state acting as a proxy for the state of neural activity.

A fundamental problem of fMRI data analysis concerns the accurate analysis of the effective functional connectivity of voxels at fine-grained spatial and temporal resolution scales, based on the acquisition capabilities of state-of-the-art neuro-imaging techniques. There are methods for functional connectivity analysis that identify undirected connectivity. But because of its complexity, a satisfactory understanding of neural mechanisms is likely to require identification of directed functional connectivity.

Linear Granger causality (GC) has been widely applied to functional MRI data analysis as a measure of causal influence. Partial Directed Coherence (PDC) has also been successfully applied as a measure of causal influence in computational neuroscience for the analysis of directed interactions between components of multivariate time series. Most popular methods of data analysis utilizing GC and PDC are linear methods based on multivariate autoregressive (MVAR) models. While PDC is directly linked to MVAR parameters, the general concepts of GC cover a family of linear approaches in addition to MVAR to define connectivity measures.

Recent work has successfully demonstrated and extended the applicability of linear GC approaches in functional MRI analysis. The likely non-linear physiological basis of the transmitted signals, however, motivates non-linear extensions of GC to better capture the underlying properties of the observed non-linear dynamic systems.

Although various non-linear extensions of GC have been proposed in the literature, such methods cannot be applied to large-scale effective connectivity analysis at a whole-brain neuroimaging voxel resolution scale. Rather, these non-linear extensions have been confined to analyzing brain connectivity in specifically simplified settings, such as pre-defined seed-based region-of-interest studies. The reasons for such restrictions were previously discussed above: besides computational expense, the extendibility to multi-variate analysis of high-dimensional dynamic systems with a low number of temporal observations involves specific challenges regarding parameter optimization of sophisticated models on limited data.

If such challenges are addressed by commonly used model simplification strategies, interactions between simplified signal components cannot be readily transferred back into the original high-dimensional space, and directed interactions between the original network nodes are not revealed. This significantly limits the interpretation of brain network activities in physiological and disease states and in response to behavioral or pharmacological intervention.

A different approach to Granger causality utilizes kernel-based learning machines that predict the next value of a time series by minimizing a risk minimizer function. Such kernel-based learning machines can be used to evaluate causality between two simultaneously acquired time series by utilizing values from both series as input variables. If the prediction error of the first series is reduced using information from the second series, then the second series can be said to have a causal influence on the first series.

It is possible to construct predictors for linear and non-linear Granger causality evaluation. However, standard statistical and machine learning approaches cannot readily be applied to large-scale fMRI data analysis because fitting multivariate time-series models to very high-dimensional data is problematical as previously described. The analysis can be limited to pre-defined regions of interest but the regions of interest may not correspond to the actual spatial distribution of relevant process components. The model complexity can be reduced but this implies inappropriate model simplifications based on ad hoc assumptions on the sparseness of the observed network. Another strategy is to reduce the dimensionality of the data, for example by Principal Component Analysis (PCA) or Independent Component Analysis (ICA). An identified interaction between two components, however, cannot be readily transferred back to the original dimensional space and so directed interactions between the original network nodes cannot be identified.

The applicant and his colleagues have developed a method for linear Granger causality analysis of large-scale fMRI data using linear MVAR modeling which circumvents the drawbacks for conventional multivariate linear Granger causality evaluation. The method (referred to as "large-scale Granger Causality" or "lsGC") introduces an invertible dimension reduction of the fMRI data followed by a back-projection of prediction residuals into the original data space. The method generates a Granger causality index or measuring the causal influence of each voxel time-series on each other voxel time-series.

The Granger causality indices generated by the lsGC method can be utilized to form a $N^2$ affinity (connectivity) matrix whose coefficients are the large-scale Granger causality indices. The underlying network structure information present in the affinity matrix can be extracted to discover high-modularity communities of voxels in the network. Network structure information can be extracted from the affinity matrix by, for example, non-metric clustering or community detection methods, such as the Louvain method or its variants, see e.g. [1], [2].

The lsGC method has been very useful for some types of functional MRI analyses, but extension of the lsGC method to non-linear causation analysis was unsuccessful. There remains a need for a method that enables the identification of non-linear causal influences between components of complex systems, such as directed interactions in full-scale fMRI data and other large-scale networks. The method should overcome the applicability restrictions of current GC techniques and enable a non-linear, directed and multivariate full-brain effective connectivity network representation for large-scale fMRI data analysis.

SUMMARY OF THE DISCLOSURE

Disclosed is a method referred to as "large-scale Extended Granger Causality" (or more briefly, "lsXGC") and related device that enables the identification of linear or non-linear causal influences between components of complex systems. The method enables linear or non-linear causality analysis of high-dimension multivariate time-series, such as, but not limited to, full-scale fMRI data. Although the method and its name (lsXGC) was initially inspired by GC-type causality analysis approaches, the disclosed method is applicable to other approaches for inferring causality, such as Mutual Connectivity Analysis (MCA), Convergent Cross-Mapping (CCM), or calculating information-theoretic measures of causation.

The lsXGC method can also be used with a multivariate features dataset for feature selection. Instead of the data being organized as a multivariate time-series containing rows of time-series, each row including temporal values (columns), the rows may be made up of features and the columns as multi-dimensional data samples, i.e. as vectors, whose elements represent the value of each feature for a given sample. Then instead of estimating the value of a target time-series to evaluate causality, the target may represent any quantity that may be estimated from the data samples.

That is, for feature selection the disclosed method can also be used to calculate measures that serve as statistical surrogates of the "causal influence" of each feature on any chosen target quantity, or vice versa. The resulting measures can be used to determine the "relevance" of each feature for estimating the target. The disclosed method when used for feature selection is especially useful in situations where the number of dimensions (features) is high, but the number of available data samples is low.

The disclosed lsXGC method is a computer-implemented method for determining a measure of the causal interdependence of a source dataset S and a target dataset Y in the simultaneous presence of a non-empty confounding dataset B, the confounding dataset B not being the source dataset S and not being the target dataset Y, the method comprising the steps of:

(a) calculating at least one of the following dimensionally modified representations (aa) and (ab):

(aa) a dimensionally modified representation $n_t$ of one of the following three datasets (1), (2), and (3): (1) the confounding dataset B, (2) the target data set Y, and (3) the union of the confounding dataset B and the target dataset Y; whereby the representation $n_t$ does not include information about the source dataset S, and (ab) a dimensionally modified representation $n_c$ of at least one of the following datasets (1), (2), (3), and (4): (1) the source dataset S, (2) the union of the source dataset S and the confounding dataset B, (3) the union of the source dataset S and the target dataset Y, and (4) the union of the source dataset S, the confounding dataset B, and the target dataset Y;

(b) constructing at least one of the following augmented dimensionally modified representations $m_t$ or $m_c$ by:

(ba) constructing an augmented dimensionally modified representation $m_t$ that does not contain information about the source dataset S by augmenting a dimensionally modified representation $n_t$ with information about at least one of the following datasets (1), (2), and (3): (1) the target dataset Y, (2) the confounding dataset B, and (3) the union of the target dataset Y and the confounding dataset B; and/or (bb) constructing an augmented dimensionally modified representation $m_c$ that contains information about the source dataset S by:

(bba) augmenting the dimensionally modified representation $n_c$ with information about at least one of the following datasets (1), (2), (3), and (4): (1) the source dataset S, (2) the confounding dataset B, (3) the target dataset Y, and (4) any union of at least two of the datasets S, B, and Y; or (bbb) augmenting the dimensionally modified representation $n_i$ or the augmented dimensionally modified representation $m_i$ with information about the source dataset S;

(c) calculating a measure of causal interdependence of the source dataset S and the target dataset Y using at least one of the augmented dimensionally modified representations $m_i$ or $m_c$, whereby information about the confounding data set B is used:
   (1) directly, or
   (2) indirectly by having the information about the confounding data set B having been included in the representations $n_i$, $n_c$, $m_i$, or $m_c$, which are used for calculating a measure of causal interdependence of the source dataset S and the target dataset Y.

In the following, a typical embodiment of the disclosed lsXGC method for analyzing a high dimensional multivariate dataset is described next.

The source dataset S and the confounding dataset B may be elements of a complete dataset $N_c$, that is, $S \in N_c$, and $B \in N_c$. The target dataset Y may or may not be an element of the complete dataset $N_c$.

A typical embodiment for a high dimensional multivariate dataset of the disclosed lsXGC method may include the following steps:

(a) calculating a dimensionally reduced representation $n_i$ of one of the following two datasets: (1) the confounding dataset B, and (2) the union of the confounding dataset B and the target dataset Y, wherein the representation $n_i$ does not include information about the source dataset S;

(b) optionally, calculating a dimensionally reduced representation $n_c$ of the union of the following datasets: (1) the confounding dataset B and the source dataset S, or (2) the confounding dataset C, the source dataset S, and the target dataset Y;

(c) calculating predicted values $\tilde{y}$ of the target dataset Y without using information about the source dataset S by
   (a) basing the calculations of $\tilde{y}$ on the dimensionally reduced representation $n_i$, or by (b) augmenting the dimensionally reduced representation $n_i$ with information about the source dataset S and basing the calculations of $\tilde{y}$ on the augmented representation of $n_i$;

(d) calculating predicted values $\hat{y}$ of the target dataset Y using information about the source dataset S by:
   (i) augmenting one of the dimensionally reduced representation $n_i$ or the dimensionally reduced representation $n_c$ with information about one of: the source dataset S, the target dataset Y, or both the source dataset S and the target dataset Y;
   (ii) basing the calculations of f on the augmented representation generated in step (i); and (e) calculating a measure of the causal influence of the source dataset S on the target dataset Y based on comparing prediction errors of the predicted values $\tilde{y}$ and the predicted values $\hat{y}$ as compared to the target dataset Y.

The datasets B, S, and Y may all be time-series datasets or may all be features datasets as discussed in more detail below.

Note that the described specific typical embodiment was chosen, because it closely matches the following discussion.

A discussion of the disclosed method as applied to causality analysis of a high dimension multivariate time-series is provided next.

Consider a multi-dimensional system $X \in \mathbb{R}^{N \times T}$ of $N \geq 3$ time-series of simultaneously measured values and T the number of temporal values of each time-series. The system X is a "complete system" $N_c$ that includes the source time-series S and one or more confounding time-series B.

The values of the complete system $N_c$ may be values obtained after pre-processing of originally measured or received values. Pre-processing of multivariate time-series can include, but is not limited to, motion-correction, linear de-trending, data normalization to zero mean and/or unit standard deviation, phase space transformation using lagged coordinates, high-/low-/band-pass filtering or wavelet operations. For methods including phase space transformation that operate on fixed-dimensional lagged coordinates, such as multivariate vector auto-regression, procedures for determining the model order, such as Bayesian Information Criterion (BIC) or Akaike Information Criterion (AIC) or others, such as based on information-theoretic measures, e.g. mutual information, may be used.

The lsXGC method calculates a measure of causal interdependence between a subset S of the time-series of the complete system $N_c$ and a target time-series Y. The time-series subset S is identified herein as the "conditional source" or "source" S, and may include more than one time series of the complete system $N_c$. The target time-series Y may be an element of the complete system $N_c$ or may be separate from and not included in the complete system $N_c$.

Application of the lsXGC method for measuring the causal influence of the source S on the target Y will be described next. Note that, for simplicity, throughout this description, for calculating dimensionally modified representations of time-series, we only consider the case of calculating dimension-reduced representations. However, note that the disclosed invention also includes the case of dimensional modification, where the dataset obtained after applying dimensional modification has a higher dimension than the original dataset. A typical example for this would include the use of kernel transformations for dimensional modification, where the number of used kernels exceeds the dimension of the original dataset.

In a first step, generate a dimension-reduced representation $n_i \in \mathbb{R}^{D \times T}$ of an incomplete system $N_i$, wherein $D < N$. The incomplete system $N_i$ is a subset of the complete system $N_c$ in that the incomplete system $N_i$ does not include the source S (that is, $N_i = N_c \setminus S$). The incomplete system $N_i$ therefore has no information about the source S, but does include at least one "confounding" time-series of $N_c$. The at least one confounding time series does not belong to the source S and does not belong to the target Y, but may influence or may be influenced by all or some of the other time-series, including the target Y.

In a second step, augment one or both of the dimension-reduced incomplete representation $n_i$ and, if generated, the dimension-reduced complete representation $n_c$ by at least one "augmenting" time-series $x_a$ that contains information about the conditional source S or about the target Y, or both the conditional source S and the target Y. An augmented dimension-reduced representation gains information about the source S and/or the target Y without a substantial increase in size or computational complexity.

The at least one augmenting time-series $x_a$ can be an element of the source S ($x_a \in Sa$) and/or the target Y ($x_a \in Y$).

Alternatively, the at least one augmenting time-series $x_a$ is a modified element of the source S and/or the target Y. For example, the at least one augmenting time-series $x_a$ can be generated by replacing the original values of a time-series element of S with the logarithms of the original values. Other modifications of the source S and/or the target Y are possible, such as for more efficient generation of causality indices in subsequent steps.

The dimension-reduced incomplete representation $n_i$ can be augmented with information about the source S to generate a source-augmented dimension-reduced incomplete representation $n_{iaS}$, information about the target Y to generate a target-augmented dimension-reduced incomplete representation $n_{iaY}$, or information about both the source S and the target Y to generate a source-and-target-augmented dimension-reduced incomplete representation $n_{iaSY}$. The dimension-reduced complete representation $n_c$ can be augmented with information about the source S to generate a source-augmented dimension-reduced complete representation $n_{caS}$, information about the target Y to generate a target-augmented dimension-reduced complete representation $n_{caY}$, or information about both the source S and the target Y to generate a source-and-target-augmented dimension-reduced incomplete representation $n_{caSY}$.

In a third step, calculate two different estimates or predictions of the target time-series Y, namely:
  (a) a first set of predictions ỹ of future values of the target Y that does not use information about the conditional source S in calculating the predictions, and
  (b) a second set of predictions ŷ of future values of the target Y that does use information about the conditional source S in calculating the predictions of the target Y.

The first set of predictions ỹ can be calculated using the un-augmented dimension-reduced incomplete representation $n_i$ or the target-augmented dimension-reduced incomplete representation $n_{iaY}$. Note neither incomplete representation includes information about the source S.

The second set of predictions ŷ can be calculated using the source-augmented dimension-reduced incomplete series $n_{iaS}$, the source-augmented dimension-reduced complete series $n_{caS}$, the target-augmented dimension-reduced incomplete series $n_{iaY}$, the target-augmented dimension-reduced complete series $n_{caY}$, the source-and-target-augmented dimension-reduced incomplete series $n_{iaSY}$, or the source-and-target-augmented dimension-reduced complete series $n_{caSY}$.

The sets of predictions of ỹ and ŷ can be generated by any mathematical linear or non-linear estimation methods using, but not limited, to supervised, non-linear machine learning algorithms.

There are no limitations to the specific estimation methods, including machine learning algorithms, used for calculating the predictions of the target values ỹ and ŷ. Besides linear estimators, such as multivariate autoregressive or affine modeling, non-linear methods may be used, such as feed-forward multi-layer perceptrons, e.g. trained by error-backpropagation, radial basis functions (RBF) neural networks or generalized radial basis functions (GRBF) neural networks, support vector regression, any linear or nonlinear regression methods, any type of local models, including local linear models or local average models, random forests, decision trees, recurrent neural networks, including, but not limited to Echo State Networks or LSTMs. Specifically, predictions may also be calculated using any type of ordinary or partial differential equation solvers. This may be specifically useful in situations, in which an ordinary or partial differential equation model is assumed for any subset of time-points of any subset of time-series of the complete system. Any combination of different modeling approaches for calculation of the estimates, including the approaches listed in this paragraph, may be used for calculating the estimates, specifically using committee machines, boosting, bootstrap aggregating, mixture-of-experts, any type of ensemble learning (ensemble methods), and/or the like.

Note also that the predictions of the target values ỹ and ŷ do not have to represent scalars or vectors that exactly match the dimension of the target. They may also represent ensembles of estimates, frequency distributions, such as represented by histograms, estimates of probability distributions and/or their parameters, which quantitatively characterize the target, such as in a statistical sense, using or not using information about the conditional source S. This includes any quantity that can be used to calculate any type of statistical or information-theoretic measures between conditional source S and target Y, such as transfer entropy, conditional mutual information, mutual information, divergences, any correlation measure, such as Spearman or Pearson correlation, partial correlation, Patel's tau, or coherence measures, such as partial directed coherence.

The fourth step is to calculate a measure of interdependence between the conditional source S and the target Y.

In a Granger causality context, this interdependence can be accomplished by calculating a measure $F_{S \to Y}$ of the causal influence of the conditional source time-series S on the target time-series Y by computing quantities that compare the agreement or errors between estimated and actual target time-series using the estimates ỹ and ŷ, such as a form of a Granger causality index $$\ln\left(\frac{\varepsilon_i}{\varepsilon_c}\right)$$

in which $\varepsilon_i$ is the variance of the residuals (ỹ−y) and $\varepsilon_c$ is the variance of the residuals (ŷ−y). Other statistical measures, such as f-statistics, or surrogate statistics, e.g. bootstrap methods, e.g. based on Granger causality indices, can be used as measures of causality $F_{S \to Y}$. Interdependence can also be calculated from information-theoretic statistical measures of interdependence, such as transfer entropy or conditional mutual information.

Discussed next is use of the disclosed lsXGC method for multivariate feature selection.

Interestingly, the lsXGC method can be adapted to serve as a novel approach to high-dimensional multivariate feature selection. This can be understood by exploiting the mathematical equivalence of causality measures, including Granger causality, and information-theoretic quantities, such as "transfer entropy". In this context, causality indices computed by the lsXGC method for multivariate time-series can be characterized as quantities representing the information flow between time-series, such as for indicating the "relevance" of a source time-series S for the local prediction of a future value of a target time-series Y in the presence of all other time-series in the system.

If the conceptual focus on time-series analysis is eliminated, however, the lsXGC method can be re-interpreted as a generic feature relevance estimation approach, such as used for feature selection, where the "relevance" of a feature S for the estimation of a quantity Y can be computed in the presence of all other features in a high-dimensional data set.

By detaching the lsXGC method from its dynamic time-series context, however, important properties related to the Granger method interpretation as a statistical surrogate for directed "causality" will be lost, because Granger causality inherently incorporates the notion of a directed timeline from the past to the future. Although a directed "causal" connection between input and output quantities cannot be asserted, such an approach is still useful as a method to determine relevant features in high dimensional feature selection problems, such as in brain network analysis. Extending the lsXGC method to feature selection is inspired by [11], which provides a detailed review of time dependency and non-temporal notions of causality for machine learning.

The disclosed lsXGC method enables linear or nonlinear causality analysis or relevance analysis between elements of a multivariate high dimensionality dataset to be performed by reducing dimensionality and by augmenting the reduced dimension representations with data relevant to elements of interest without a substantial increase in size or complexity, thus enabling efficient analysis of large or even underdetermined multivariate systems.

Other objects and features of the disclosure will become apparent as the description proceeds, especially when taken in conjunction with the accompanying drawing sheets illustrating one or more illustrative embodiments.

DETAILED DESCRIPTION

Figure 1:
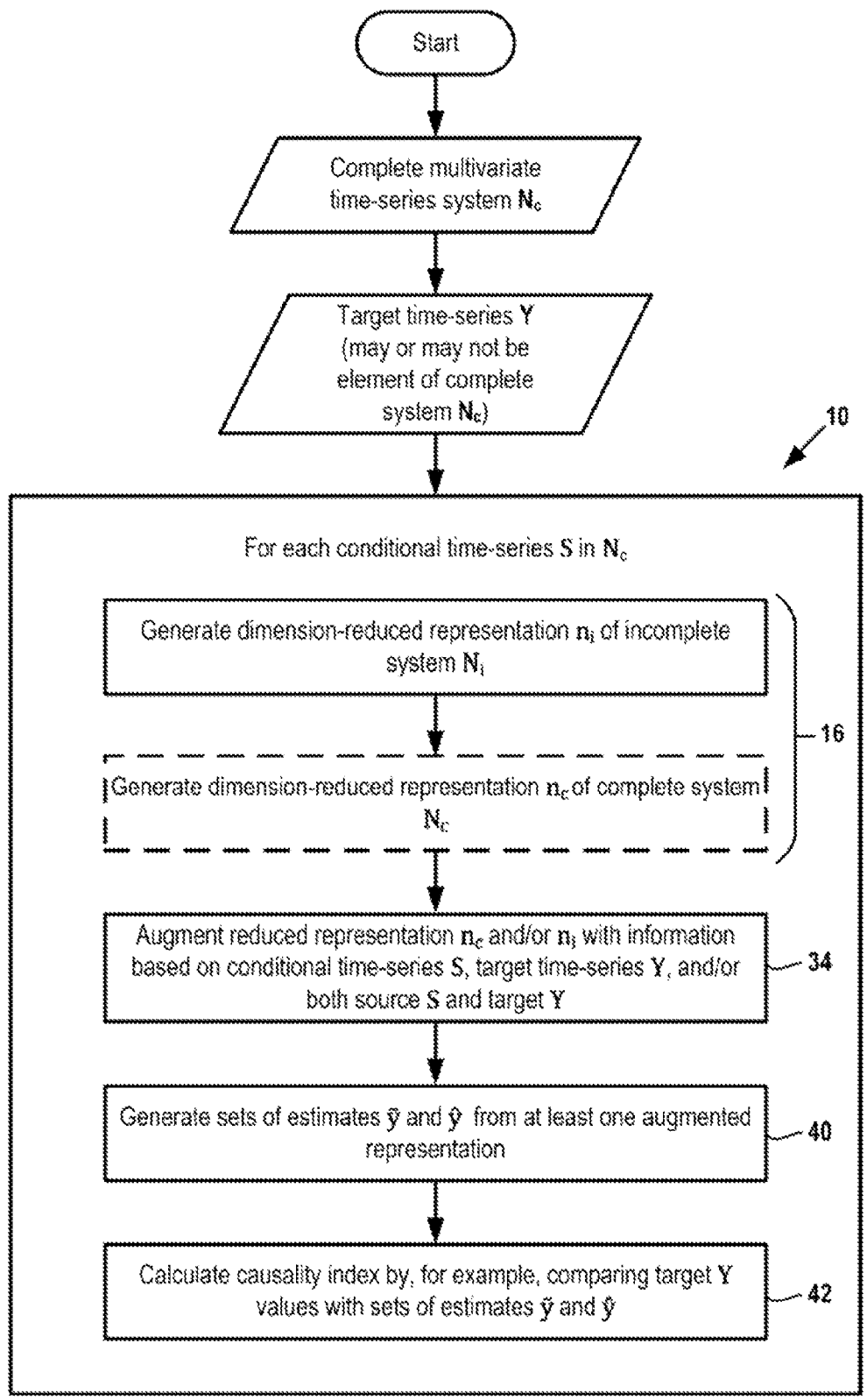
FIG. 1 is a flow chart showing major steps of the disclosed lsXGC method.

FIG. 1 illustrates the main steps of the lsXGC method 10 as applied to a high-dimension multivariate time-series dataset 12. The dataset defines a complete multivariate time-series system $N_c \in \mathbb{R}^{N \times T}$ having simultaneously measured values. The complete system $N_c$ includes as a subset one or more time-series defining a conditional source time-series or source S. It is desired to evaluate the causal influence of each source S on a dataset 14 defining a target time-series or target Y having values simultaneously measured with those of the complete series $N_c$. A source S may include more than one row of the N rows of $N_c$. The target Y may or may not be an element or subset of the complete system $N_c$.

Figure 2:
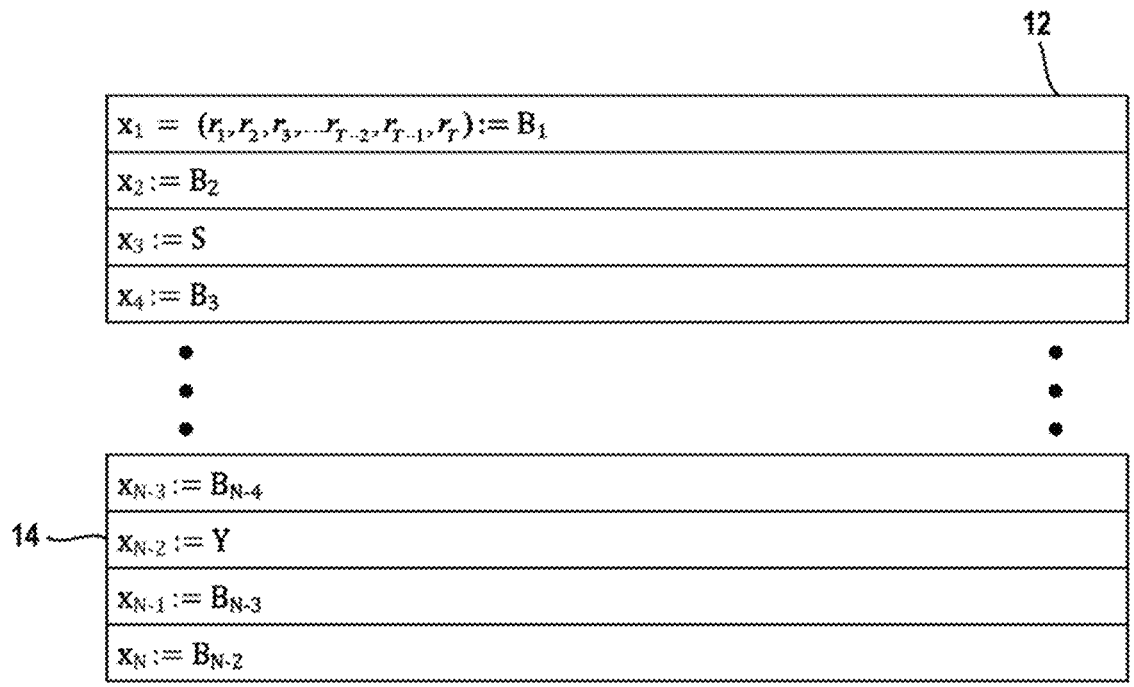
FIG. 2 illustrates a complete multivariate system to be analyzed for source to target causality using the lsXGC method.

FIG. 2 illustrates the dataset 12 defining the complete system $N_c$ that includes N time-series $x_1, x_2, x_3, \ldots, x_{N-3}, x_{N-2}, x_{N-1}$, and $x_N$. Each time-series is a series of T data points indexed or stored in time order. FIG. 2 illustrates the members of the time-series $x_1 = (r_1, r_2, r_3, \ldots, r_{T-2}, r_{T-1}, r_T)$ listed in time order. Most commonly, a time series is a sequence taken at successive equally spaced points in time.

In the illustrated application of the lsXGC method the source time-series S is the time-series $x_3$ and the target time-series Y is an element of the complete system $N_c$, namely the time-series $X_{N-2}$. It is desired to evaluate the causal influence $F_{S \to Y}$ of the source time-series $x_3$ on the target time-series $x_{N-2}$. The other time-series of the complete system $N_c$ are confounding time-series B that do not belong to the source S and do not belong to the target Y but may influence or may be influenced by all or some of the other time-series, including the target Y.

In the first lsXGC step 16 (see FIG. 1), generate a dimension-reduced representation $n_i$, $n_i \in \mathbb{R}^{D \times T}$ of an incomplete system $N_i$ and, optionally, generate a dimension-reduced representation $n_c \in \mathbb{R}^{E \times T}$ of the complete system $N_c$ wherein D, E<N. The incomplete system $N_i$ is the system created from the complete system $N_c$ by removing the source S from the complete system $N_c$, that is, $N_i = (N_c \setminus S) \in \mathbb{R}^{F \times T}$ wherein F<N. As explained in more detail below, the dimension-reduced incomplete system representation $n_i$ can be generated either by direct dimensionality reduction of the incomplete system $N_i$ or by dimensionality reduction of the complete system $N_c$ and additional, such as subsequent, elimination of information about the source time-series S.

Dimensionality reduction of the incomplete system $N_i$ or of the complete system $N_c$ can be performed using linear dimensionality reduction techniques, such as Principal Component Analysis (PCA), or non-linear techniques. Principal Component Analysis is a linear technique that transforms the original dataset into its principal components by transforming the dataset into a lower-dimensional subspace. The first principal component explains the greatest amount of the variance in the data, the second principal component explains the second greatest amount of variance, and so on. A plot of explained variance versus the number of principal components can be used in Principal Component Analysis to determine a reasonable number of principal components and hence the dimensionality of the reduced-dimension incomplete representation $n_i$ or the optional reduced-dimension complete representation $n_c$.

For non-linear dimensionality reduction methods, one can utilize my previous work on information visualization by non-linear dimension reduction disclosed in my U.S. Pat. No. 7,567,880 as well as a wide scope of non-linear algorithms available from the literature, see e.g. [3]. These include machine learning techniques for dimensionality reduction, such as autoencoders and their variants (e.g. variational autoencoders), clustering methods (e.g. k-means, fuzzy c-means, self-organizing maps (SOM), divergence-based methods, such as stochastic neighbor embedding (SNE), independent component analysis (ICA), exploratory observation machines (XOM), as well as variants or combinations thereof.

The dimension-reduction algorithm used does not have to be invertible. The original target time-series Y can be estimated directly from the dimension-reduced system and does not have to be estimated indirectly from back-projecting an estimate of the dimension-reduced time-series into the original space as is performed using the large scale Granger Causality (lsGC) method, although such back-projection of estimates calculated in the dimension-reduced space can be used with lsXGC as well.

Generating the dimension-reduced incomplete system $n_i$ is described next.

Figure 3:
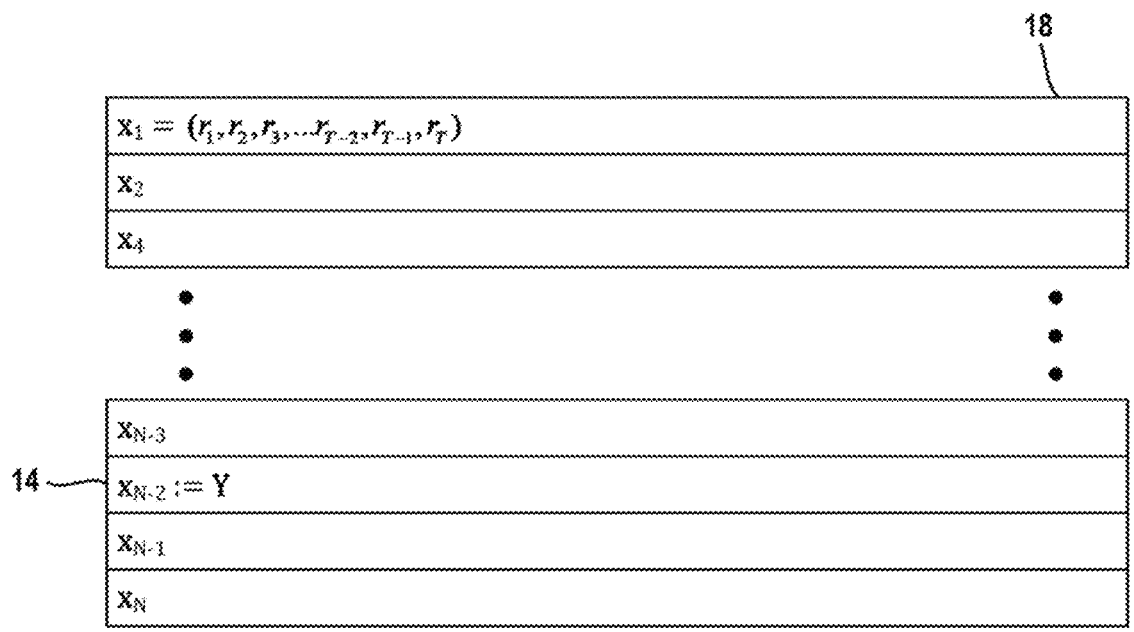
FIG. 3 illustrates an incomplete multivariate system generated by removing the source data elements from the complete system shown in FIG. 2.

FIG. 3 illustrates the dataset 18 of the incomplete system $N_i$ generated by removing the source S, i.e., $x_3$, from the complete system $N_c$. The incomplete system $N_i$ must include at least one confounding time-series that is not an element of the source S or the target Y. The illustrated dataset 18 includes the confounding time-series $x_1$, $x_2$, $x_4$, ..., $x_{N-3}$, $x_{N-1}$, and $x_N$ (the target Y is not considered to be a confounding time-series).

Figure 4:
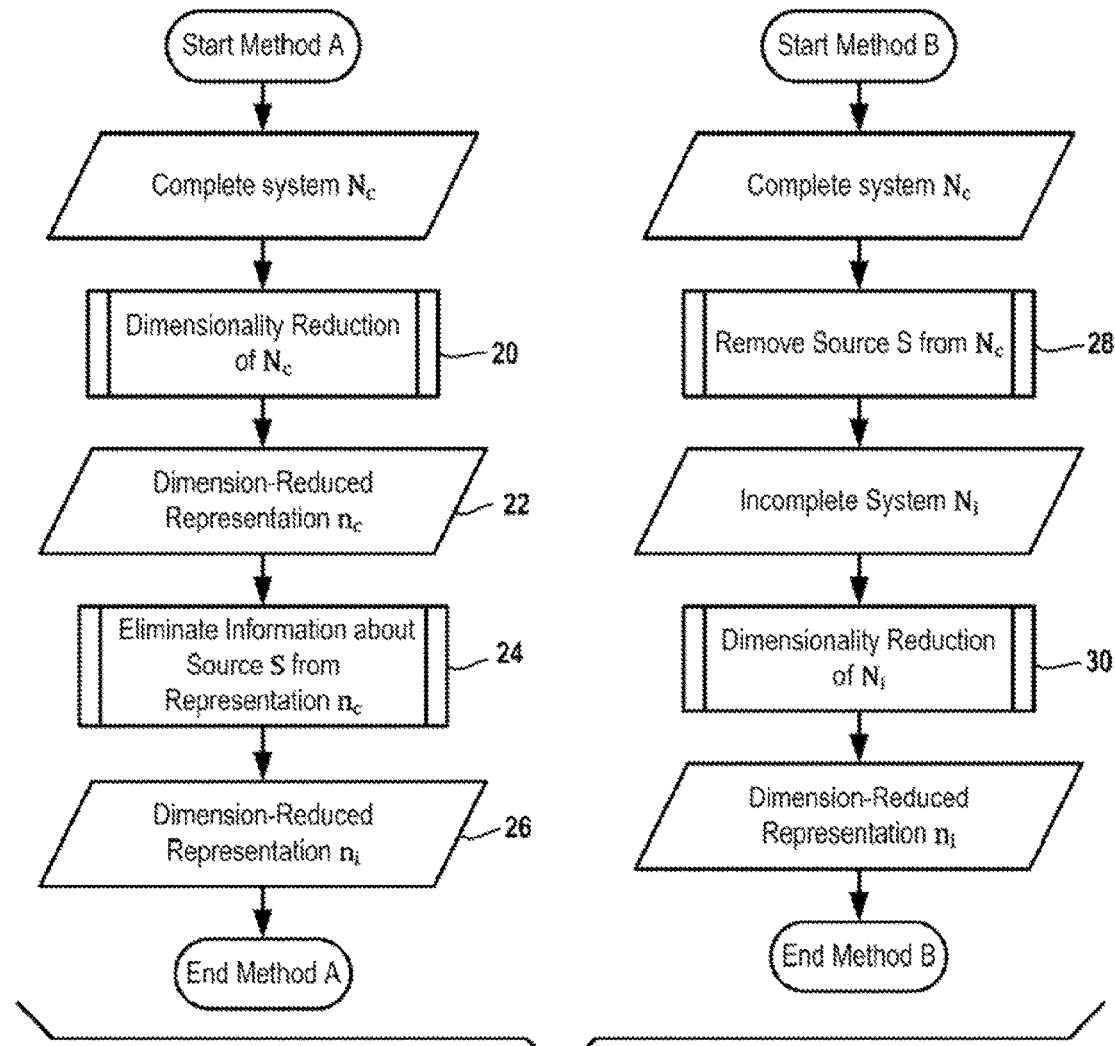
FIG. 4 illustrates alternative methods A and B for generating a dimension-reduced representation of the incomplete system shown in FIG. 3.

There are two alternative methods for generating the dimension-reduced representation $n_i$ of the incomplete system $N_i$. These alternative methods are illustrated in FIG. 4. One alternative method ("Method A") generates the dimension-reduced incomplete representation $n_i$ through dimensionality reduction of the complete system $N_c$ and without generating the incomplete system $N_i$ directly. The other alternative method ("Method B") generates the incomplete system $N_i$ and then generates the dimension-reduced incomplete representation by dimensionality reduction of the incomplete system $N_i$ directly.

Referring to FIG. 4, in the first alternative method ("Method A"), perform dimension reduction of the complete system $N_c$ in a first step 20 to generate a dataset 22 that is the dimension-reduced representation of the complete system (referred to herein as $n_c$). In a second step 24 eliminate information about the conditional source time-series S from the representation $n_c$ to generate the dataset 26 defining the dimension-reduced representation of the incomplete system $n_i$.

There are various ways to eliminate information of the source S from $n_c$ to generate $n_i$, depending on the specific dimension reduction algorithm used.

For example, if Principal Components Analysis (PCA) is used to generate the dimension-reduced complete representation $n_c$, all entries in the coefficient transformation matrix that correspond to the input dimension(s) of the conditional source time-series S can be set to zero. If kernel transformations are used for dimension reduction, such as based on clustering methods, all contributions to calculating the kernel-transformed time-series originating from the input dimensions of the conditional source time-series S can be set to zero. If trained supervised neural networks are used for dimension reduction, such as auto-encoders, all network inputs related to the input dimensions of the conditional source time-series S can be set to zero. Various approaches to eliminating information about the conditional source time-series S (or target time-series Y, discussed later below) after performing dimension reduction have been described in the literature discussing large-scale Granger causality (lsGC), such as [1], [2], and the literature cited therein.

Note that if Method A is used, it is not necessary to generate the incomplete system $N_i$. Also note that if Method A is used, different dimension-reduced incomplete representations $n_i$ for different source time-series S of the complete system $N_c$ can be generated by performing step 24 of FIG. 4 for each different source time-series S using the initially generated dimension-reduced complete representation $n_c$ calculated in step 20.

So, for example, if an analyst wishes to analyze the causal influence of different conditional sources S on a given target T of a complete system $N_c$, Method A permits that the dimensionality reduction of the complete system $N_c$ is performed only once for all the possible conditional sources S of the given target T in the system. Besides the potentially desirable stability of the dimensionality reduction result, this provides significant computational advantages, specifically when large, i.e. high-dimensional, systems (such as those from full-brain fMRI) need to be analyzed with regards to causal influences among their components.

Referring again to FIG. 4, in the second alternative method ("Method B"), generate the incomplete system $N_i$ by removing the source S from the complete system $N_c$ in a first step 28 to form the incomplete system $N_i$ and then perform dimension reduction of the incomplete system $N_i$ directly in the second step 30. Because the incomplete system $N_i$ has already had the information of conditional source time-series S removed from it, no further processing of the resulting dimension-reduced representation $n_i$ is required.

Figure 5:
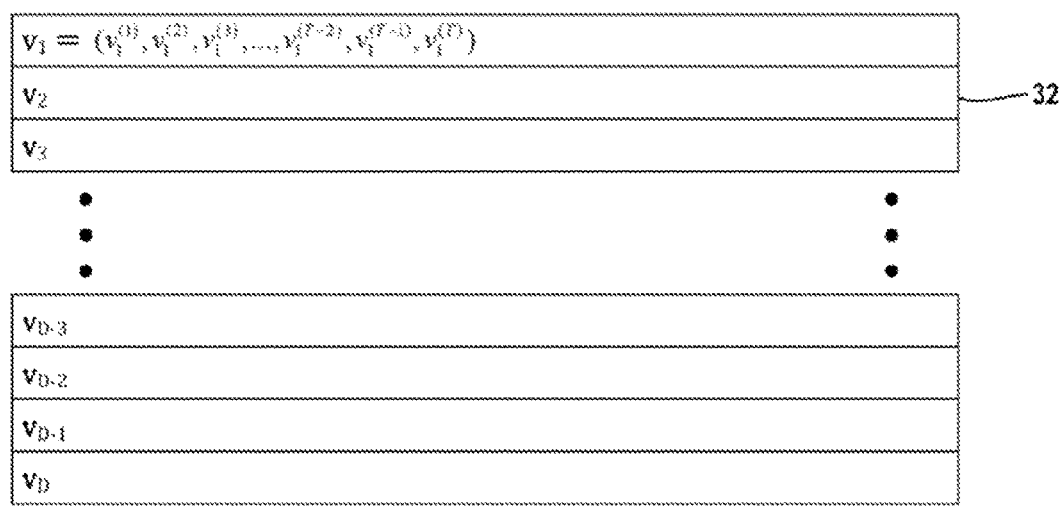
FIG. 5 conceptually illustrates the dimension-reduced representation of the incomplete system shown in FIG. 3.

As a specific example, FIG. 5 conceptually illustrates the dimension-reduced incomplete representation $n_i$ 32, such as obtained after using PCA or any other dimensionality reduction method. As explained above, the representation $n_i$ does not include information about the source time-series S. Note that $n_i$ may or may not include information about the target time-series Y, such as depending on whether Y is or is not an element of the complete system $N_c$. Note that the representation $n_i$ in FIG. 5 contains D<N time-series $v_k = (v_k^{(1)}, v_k^{(2)}, v_k^{(3)}, \ldots, v_k^{(T-2)}, v_k^{(T-1)}, v_k^{(T)})$, where k=1, ..., D. Note also that, in general, each of the time-series $v_k$ contains a mixture of information originating from several or all of the original time-series of the incomplete system.

In a second step 34 of the lsXGC method (see FIG. 1), the reduced-dimension incomplete representation $n_i$ and/or the reduced-dimension complete representation $n_c$ is augmented with information based on the conditional source S, the target Y, and/or both the conditional source S and the target Y. An augmented dimension-reduced representation $n_i$ or $n_c$ gains information about the source S and/or the target Y without a substantial increase in dimensionality, i.e. without substantial increase in size of the data set or required computational complexity. One or both of the augmented reduced-dimension representations will be used to predict the values of the source Y in a later step.

The at least one augmenting time-series $x_a$ can be an element of the source S ($x_a \in S$) and/or the target Y ($x_a \in Y$). Alternatively, the at least one augmenting time-series $x_a$ is a modified element of the source S and/or the target Y. For example, the at least one augmenting time-series $x_a$ can be generated by replacing the original values of the source S with the logarithms of the original values. Arbitrary other modifications of the source S and/or the target Y are possible, such as for more efficient generation of causality indices in subsequent steps.

Figure 6:
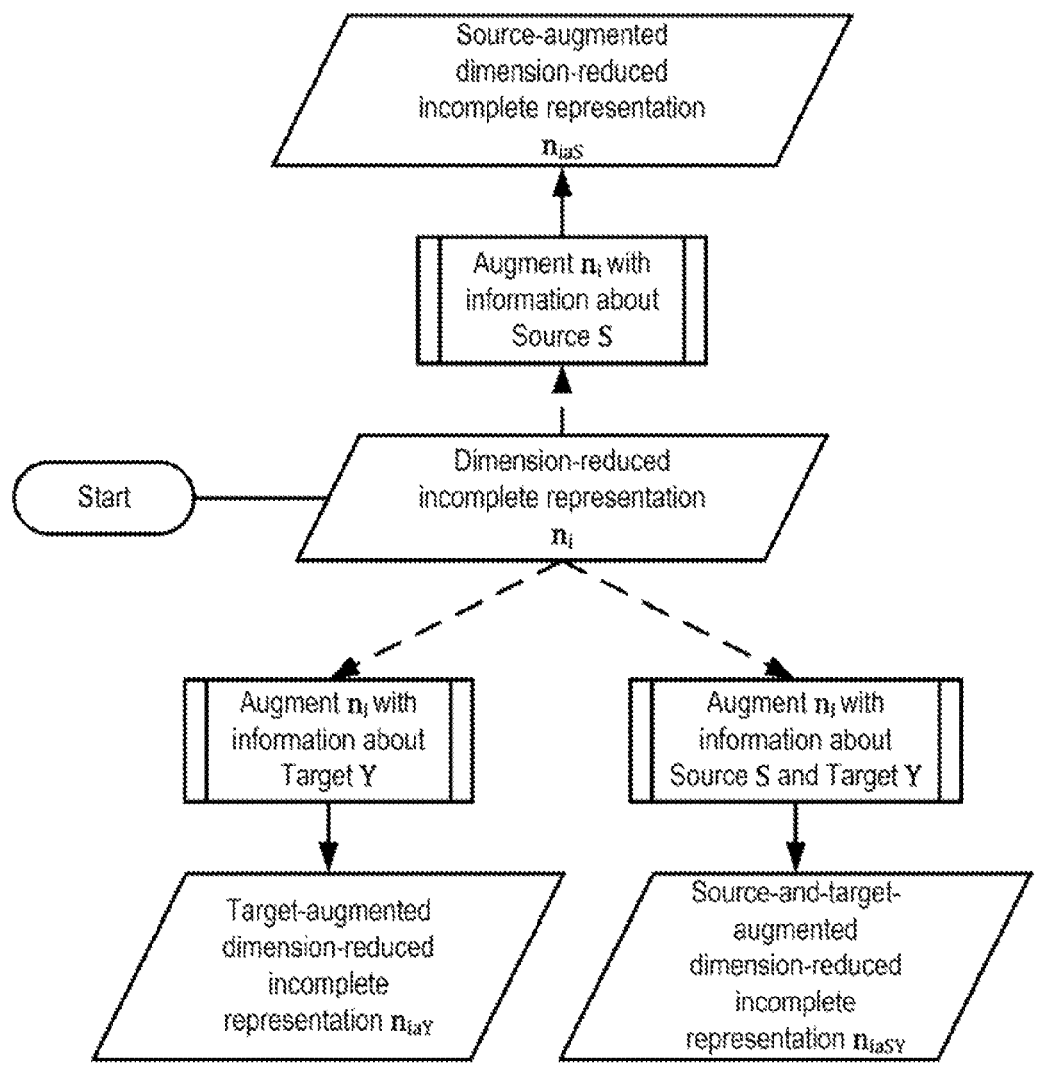
FIGS. 6 and 7 illustrate alternative methods for augmenting the dimension-reduced incomplete representation shown in FIG. 5.

As shown in FIG. 6 in which dashed arrows represent alternative Boolean-inclusive "or" paths, the dimension-reduced incomplete representation $n_i$ can be augmented with information about the source S to generate a source-augmented dimension-reduced incomplete representation $n_{iaS}$, information about the target Y to generate a target-augmented dimension-reduced incomplete representation $n_{iaY}$, or information about both the source S and the target Y to generate a source-and-target-augmented dimension-reduced incomplete representation $n_{iaSY}$.

Figure 7:
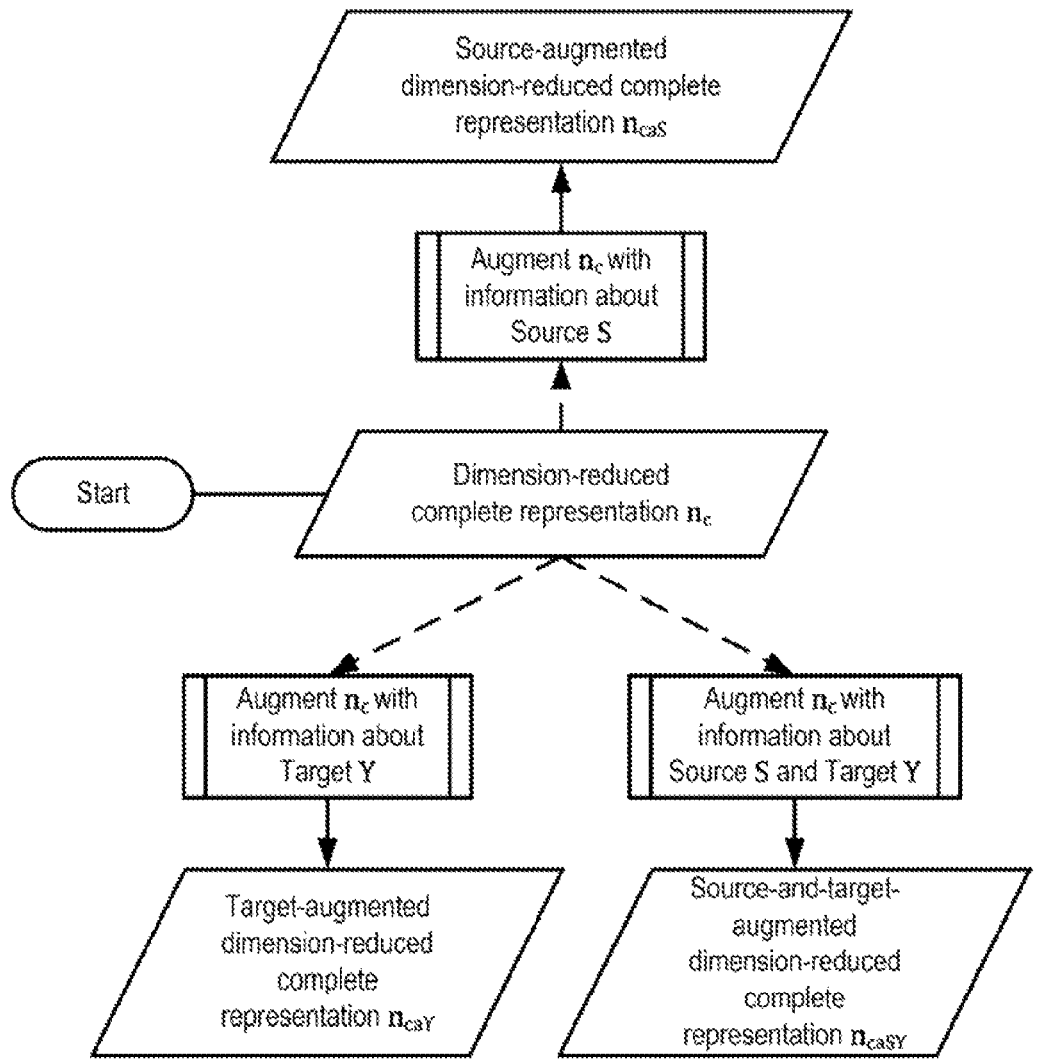

As similarly shown in FIG. 7 the dimension-reduced complete representation $n_c$ can be augmented with information about the source S to generate a source-augmented dimension-reduced complete representation $n_{caS}$, information about the target Y to generate a target-augmented dimension-reduced complete representation $n_{caY}$, or information about both the source S and the target Y to generate a source-and-target-augmented dimension-reduced complete representation $n_{caSY}$.

At least one augmented representation of the dimension-reduced incomplete representation $n_i$ or of the dimension-reduced complete representation $n_c$ will be used in the next step of the lsXGC method to estimate the target Y for causal analysis. In this embodiment of the lsXGC method a source-augmented dimension-reduced incomplete representation $n_{iaS}$ will be used for estimating the target Y using information about the source S. The incomplete representation $n_i$ will be used for predicting the target Y without using information about the source S.

Figure 8:
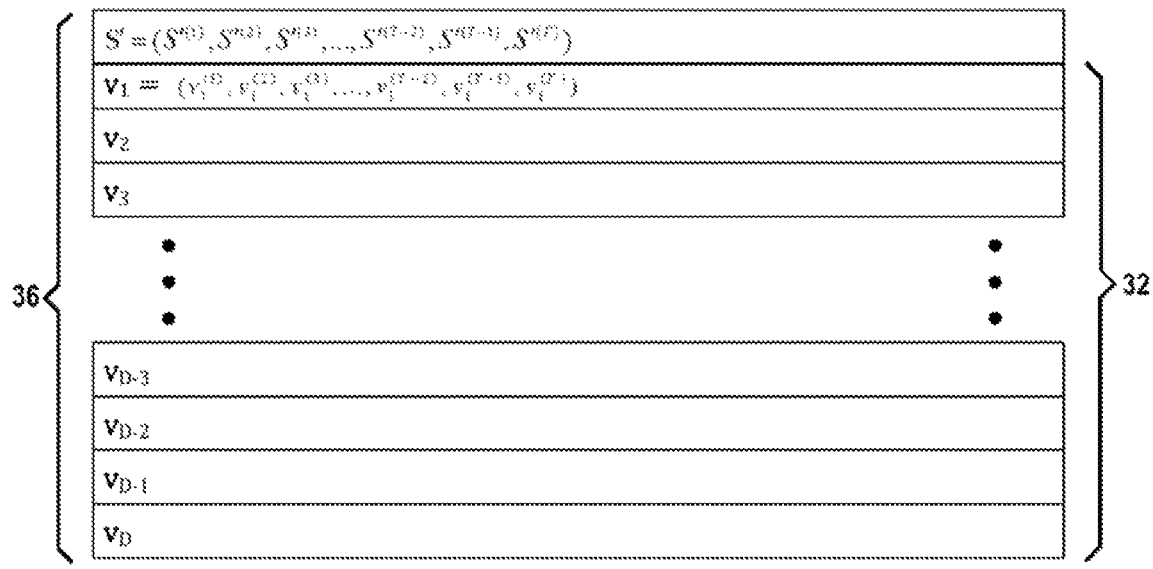
FIG. 8 conceptually illustrates the dimension-reduced incomplete representation shown in FIG. 5 augmented with information about the target time-series Y.

FIG. 8 conceptually illustrates the dataset 32 of the dimension-reduced incomplete representation $n_i$ augmented to generate a dataset 36 that defines a source-augmented dimension-reduced incomplete representation $n_{iaS}$. The incomplete representation $n_i$ is augmented with data S' that has information about the source S. A simple example would be to augment $n_i$ with the source time-series S directly, i.e., S'=S. As a result of augmentation, the source-augmented representation $n_{iaS}$ includes information about the source S that is not included in the non-augmented incomplete representation $n_i$. The source-augmented incomplete representation $n_{iaS}$ will be used for predicting the target time-series Y using information about the source S. The incomplete system $n_i$ will be used for predicting the target time-series Y without using information about the source S.

In a third step 40 of the lsXGC method (see FIG. 1) calculate:
  (a) a first set of predictions ŷ of future values of the target Y using the incomplete system $n_i$ having no information about the conditional source S, and
  (b) a second set of predictions ŷ of future values of the target Y using the source-augmented representation $n_{iaS}$ having information about the conditional source S.

Figure 9:
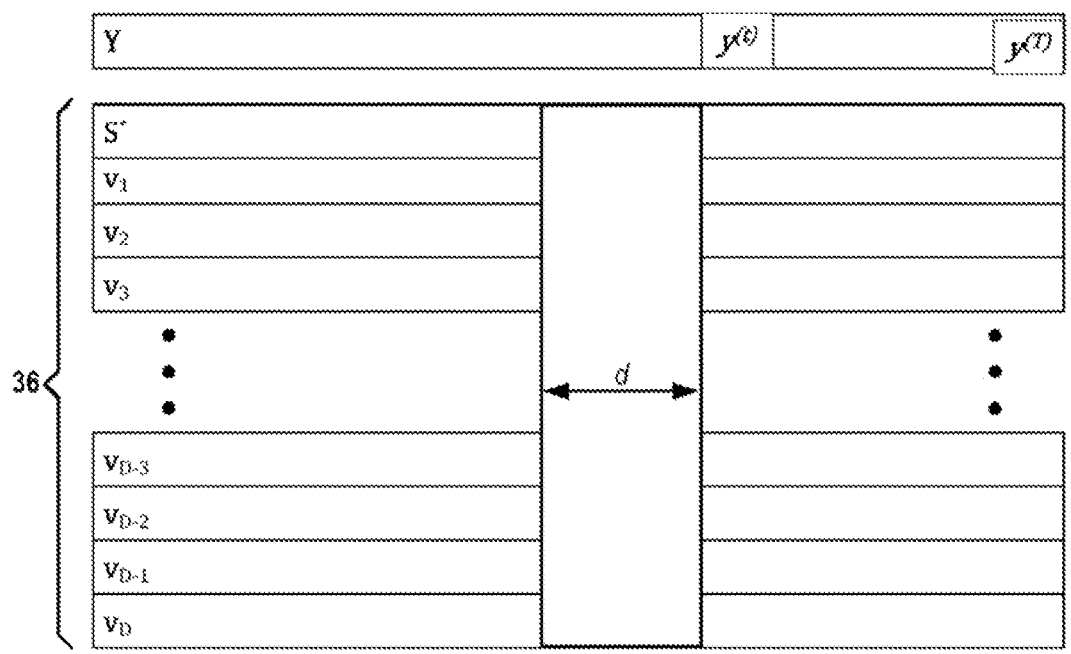
FIG. 9 illustrates calculating predictions of the target time-series using the "sliding window" technique.

FIG. 9 illustrates use of the "sliding window" technique for structuring time-series data for supervised machine learning or other mathematical modeling, including but not limited to autoregressive or affine modeling, local models, linear or non-linear regression methods, to generate the set of predictions f. Note, however, that other techniques for time-series estimation that do not require fixed-length sliding windows, such as recurrent neural networks, including, but not limited to Echo State Networks (ESN) or Long Short-Term Memory (LSTM), may be used as time-series estimators as well. In the classical Granger causality setting using the sliding window example of FIG. 9, a number d of previous time-lagged values of all the time-series of the dataset 36 of the source-augmented incomplete representation $n_{iaS}$ are used as input variables for a prediction model that is used to predict a future value, e.g. the next, value $y^{(t)}$ of the target Y, where the sliding window W is a matrix of size $(D+1) \times d$, with d the temporal width of the sliding window and D the number of time-series in the dimension-reduced incomplete system $n_i$, and $(D+1)$ the number of time-series in the source-augmented dimension-reduced system $n_{iaS}$ in the special case that the dimension of the time-series S' carrying information about the source S that is used to augment $n_i$ for creating $n_{iaS}$ is one-dimensional. Let $w^{(t)}$ represent the column vector of W for time t. Then, a typical embodiment of a linear time-series prediction model can be an affine model, e.g., $y^{(t)} = b_0 + \Sigma_{\tau=1}^{d} b_\tau \cdot w^{(t-\tau)}$, where $b_0$ is a bias coefficient, $b_\tau$ are coefficient vectors of dimension (D+1) and "·" represents the scalar product based on element-wise multiplication. The model coefficients $b_0$ and $b_\tau$ can be calculated by suitable optimization techniques, such as least squares optimization for estimating $y^{(t)}$. Other linear time-series prediction models include, but are not limited to MVAR models used on augmented or non-augmented dimension-reduced representations of the complete or incomplete system, where the MVAR predictions belonging to the time-series of the non-augmented dimension-reduced representations are used for estimating $y^{(t)}$, such as by using inverse PCA in a similar way as in large-scale Granger Causality (lsGC). Other variants of the method are possible, such as a multi-step modeling approach, wherein (i) estimates, such as predictions, for values of the augmented and/or non-augmented dimension-reduced representations are calculated by any linear or non-linear modeling method, and (ii) such estimates are used for calculating estimated, e.g. predicted, values of the target dataset Y.

In the embodiment of FIG. 9, the sliding window technique with a fixed window width d generates the predictions $\hat{y}^{(t)}$, t=d+1, ..., T of the set of predictions f using the source-augmented representation $n_{iaS}$. The sliding window technique is also used to generate the set of predictions ŷ using the dimension-reduced representation $n_i$ of the incomplete system.

Nonlinear estimation models, such as for time-series prediction, may be used as well. Variants of lsXGC, in which nonlinear estimation models are used, will be called large-scale Nonlinear Granger Causality (lsNGC). A typical embodiment would be to use Radial Basis Functions (RBF) or Generalized Radial Basis Functions (GRBF) neural networks. Here, a typical embodiment would include dimensionality reduction of the complete or incomplete original time-series system by clustering of extracted state-space vectors using a sliding window approach. The extracted windows represent state-space vectors that can be processed using clustering techniques, such as k-means, fuzzy c-means, self-organizing maps, agglomerative clustering or any clustering method known from prior art. As an example for state space clustering, let Q be a q-dimensional time-series of length T, such as the complete or the incomplete system, or the source or the target time-series, or any other one- or multidimensional time-series considered in this description, such as dimension-reduced and/or augmented complete or incomplete systems. Then sliding windows U(t) of size q×e can be extracted from time-series Q for each time t with t=e, ..., T, with e the temporal width of the sliding window. The q×e-dimensional vectors U(t) can be clustered yielding K cluster prototype vectors, e.g. cluster centers, $U_k$ of dimension q×e with k=1, ..., K. The computed cluster prototype vectors $U_k$ can then be used to obtain processed time-series representations, which contain information about the original time-series Q. A simple way to generate such processed time-series representations is to perform nonlinear kernel transformations of the original time-series, which exploit a distance measure between the values of a given time-series and each cluster center. In the above state-space clustering example for the originally q-dimensional time-series Q, one may compute a K-dimensional processed time-series $Q'(t) = (Q_1'(t), ..., Q_k'(t), ..., Q_K'(t))^T$ by using a Gaussian (Radial Basis Functions, RBF) kernel, i.e., $Q_k'(t) = \exp(-((U(t)-U_k)^2/(2\sigma^2)))$ with kernel width σ, or using a normalized Gaussian (Generalized Radial Basis Functions, GRBF) kernel, i.e., $Q_k''(t)=(1/\Sigma)Q_k'(t)$ with $\Sigma=\Sigma_{k=1}^k Q_k'(t)$.

For example, a dimension-reduced representation $n_i=Q'$ of the incomplete system shown in FIG. 5 may be obtained by state-space clustering of the incomplete system (corresponding to Method B in FIG. 4) or state-space clustering of the complete system with subsequent elimination of information about the conditional source time-series, such as by setting all contributions originating from the conditional source time-series to zero (corresponding to Method A in FIG. 4). Similarly, state-space clustering of the source or target time-series may be used to obtain processed, possibly multi-dimensional, time-series, which contain information about the source time-series or the target time-series. Using the example of FIG. 8, such processed time-series S' containing information about the source time-series may be used to augment the dimension-reduced representation $n_i=Q'$ of the incomplete system in FIG. 5 to obtain a source-augmented dimension-reduced representation of the incomplete system according to FIG. 8. Performing least-squares optimization on such a system for predicting a future, e.g. the next, value ŷ of the target time-series using a sliding window of width one and an affine model, as explained above, is equivalent to training the output weights of Radial Basis Functions (RBF) neural networks, if a Gaussian (RBF) kernel had been used to perform above nonlinear kernel transformation using state-space clustering of the original time-series. For example, one can calculate $$\hat{y}=a_0+a_1 \cdot Q'+a_2 \cdot S', \quad (1)$$

where model coefficients $a_0$, $a_1$, and $a_2$ can be estimated by least-squares optimization, and "·" represents the scalar product based on element-wise multiplication. Here, as well, the equivalent sliding window technique and affine modeling can also be used to generate the set of predictions ỹ using the dimension-reduced representation $n_i=Q'$ of the incomplete system only, i.e. without information about the source time-series S, such as by computing $$\hat{y}=b_0+b_1 \cdot Q', \quad (2)$$

where model coefficients $b_0$ and $b_1$ can be estimated using least-squares optimization.

Note that instead of RBF or GRBF models, it is straightforward to use other non-linear modeling approaches, such as local models, e.g. [5] or [12], or multivariate non-linear regression techniques.

In a fourth step 42 of the lsXGC method (see FIG. 1) calculate a measure of causal interdependence, such as a causality index $F_{S \rightarrow Y}$, e.g. by comparing target Y values with sets of predictions ỹ and ŷ. Calculation of the Granger causality index was previously described. Another useful causality index $F_{S \rightarrow Y}$ is the f-statistic:

In the above example, the f-statistic can be obtained by recognizing that the two models, equations (1) and (2) above, can be characterized as an unrestricted model and a restricted model, respectively. Residual sum of squares (RSS) of the restricted model, $RSS_R$, and residual sum of squares of the unrestricted model, $RSS_U$, are obtained. Let n be the number of vectors, and $p_U$ and $p_R$ the numbers of parameters to be estimated for the unrestricted and the restricted model, respectively. For the example of equations (1) and (2) using state space clustering with K clusters for calculating $n_i=Q'$, and S clusters for calculating S', in (2) and (1), $p_R=K$, and $p_U=K+S$, respectively. Given these settings, the f-statistic lsXGC causality index $F_{S \rightarrow Y}$ is given by:

$$F_{S \rightarrow Y} = \frac{(RSS_R - RSS_U)/(p_U - p_R)}{(RSS_U)/(n - p_U - 1)}$$

Application of the lsXGC method for causal analysis between time-series of a high-dimensional multivariate functional MRI (fMRI) dataset is described next.

Figure 10:
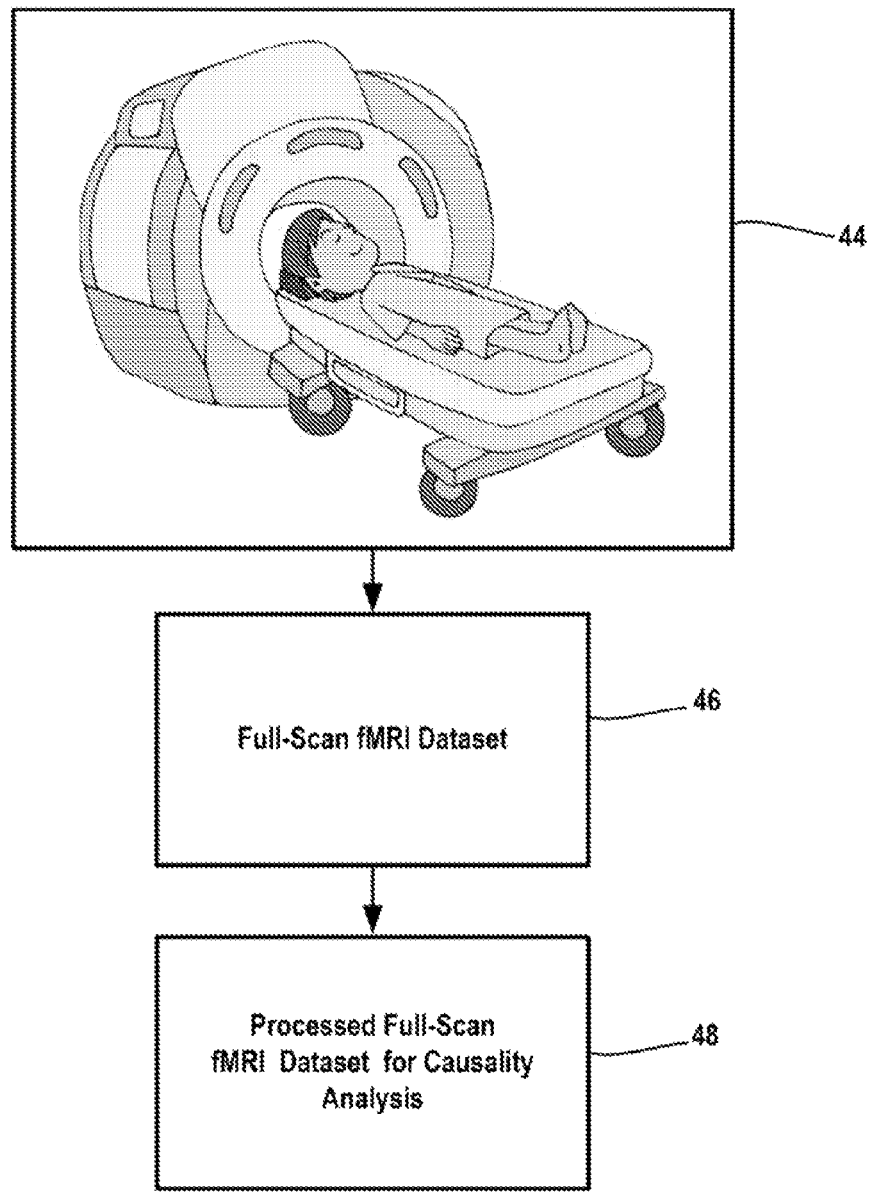
FIG. 10 schematically illustrates generation of a complete system of fMRI multivariate time-series data for causality analysis.

FIG. 10 schematically illustrates an MRI scanner 44 that generates a raw whole brain fMRI multivariate voxel time-series dataset 46. It is desired to obtain a measure of causal influence between every pair of voxel time-series.

An exemplar whole brain fMRI multivariate time-series dataset is composed of 100,000 voxels (volume pixels) within the brain that are sampled every 0.5 seconds for four minutes. The resulting fMRI dataset is a time-series $X \in \mathbb{R}^{(100,000 \times 480)}$. Note that the number of voxels, sampling rate and time period used to collect fMRI data varies depending on the MRI scanner used, age and physical condition of the subject, and other variables. The fMRI dataset is a high-dimensional multivariate time-series having a relatively low number of temporal time values, that is, 100,000 time-series of length 480.

The raw fMRI dataset 46 is pre-processed before analysis to generate a complete fMRI dataset 48 or complete system $N_c \in \mathbb{R}^{N \times T}$ that is used for causal analysis. Pre-processing may include, but is not limited to motion correction, removing a limited number of the initial values of the time-series to remove the effects of initial saturation, linear de-trending by high-pass filtering to remove effects of signal drifts, and normalizing the data to zero mean and unit standard deviation to focus on signal dynamics rather than amplitude.

It is desired to quantify the causal influence of each time-series of the complete system $N_c$ on each of the other time-series of the complete system $N_c$ for generating a $N^2$ affinity (connectivity) matrix. The analysis requires iterating through each time-series (row) of the complete system $N_c$ and having that time-series be a conditional source S or a target Y and, for that time-series, iterate through each time-series as the target Y or the conditional source S to evaluate the causal influence $F_{S \rightarrow Y}$ of the source S on the target Y for that pair of time-series, the other time-series being confounding time-series. Note that, as a special case, the target and source time-series can be identical, i.e. S=Y for evaluating the causal influence of a time-series on itself. This special case is often referred to in the context of so-called "Granger autonomy" in prior art. The analysis is illustrated in the following pseudocode in which each row of the complete system $N_c$ is selected as the target time-series Y and each time-series is selected as the conditional source time series S:

FOR each time-series x E N,
  Target Y:=x
  FOR each time-series x E N,
    Conditional Source S:=x'
    Calculate causality index $F_{S \rightarrow Y}$ by lsXGC method (previously described above)
      Step 1—generate dimension-reduced representation(s)
      Step 2—augmentation of dimension-reduced representation(s)
      Step 3—generate predictions ỹ and ŷ from augmented representation(s)
      Step 4—calculate causality index $F_{S \rightarrow Y}$ using sets of predictions ỹ and ŷ
    Store $F_{S \rightarrow Y}$ as element in $N^2$ affinity matrix
ENDFOR

ENDFOR

For fMRI causality analysis, Method A (FIG. 4) is usually preferred for generating the dimension-reduced representation $n_j$. Specifically, if one wants to analyze the causal influence of different conditional sources S of a complete system $N_c$ on a given target T, the dimensionality reduction of the complete system $N_c$ needs to be performed only once for all the possible conditional sources S of the given target T. Besides the potentially desirable stability of the dimensionality reduction result, this provides significant computational advantages, specifically when large, i.e. high-dimensional, systems such as fMRI multivariate data need to be analyzed with regards to causal influences among their components.

The performance of the lsXGC method (specifically in its non-linear lsNGC variants) was also evaluated and compared to other methods using synthetic data with known connectivity structure. The performance of these methods to unveil known connectivity relationships can be evaluated using Receiver Operating Characteristic (ROC) analysis to quantitatively compare performance. The lsNGC method was found to perform better than current state-of-the-art analysis using Convergent Cross Mapping (CCM) [5] with a high statistical significance.

The applicant has also found in using the lsNGC method for causality analysis of fMRI datasets and synthetic data that the time-series modeling approaches, e.g. supervised machine learning methods using the non-linear transformation functions, e.g. Q' and S' in the above example, do not have to be IIV invariant to generate useful results. That is, although IIV invariance is mathematically relevant, its relevance to real-world causality analysis of high dimensionality multivariate datasets is not so clear. It is suggested that data analysts use and compare both IIV invariant methods and IIV non-invariant modeling methods before settling on the machine learning or statistical modeling method to be used for lsNGC analysis of their datasets.

Application of the disclosed lsXGC method for feature selection is discussed next.

Analogies between causality analysis of multivariate time-series data and features using the lsNGC method is set out in Table 1:

TABLE 1

| Description | Time-Series | Features |
| --- | --- | --- |
| Components | Time-Series | Features |
| Number of Components | N | N |
| Number of Values of each Component | T | T |
| Relationship between Components | Causality index | Relevancy score |

Figure 11:
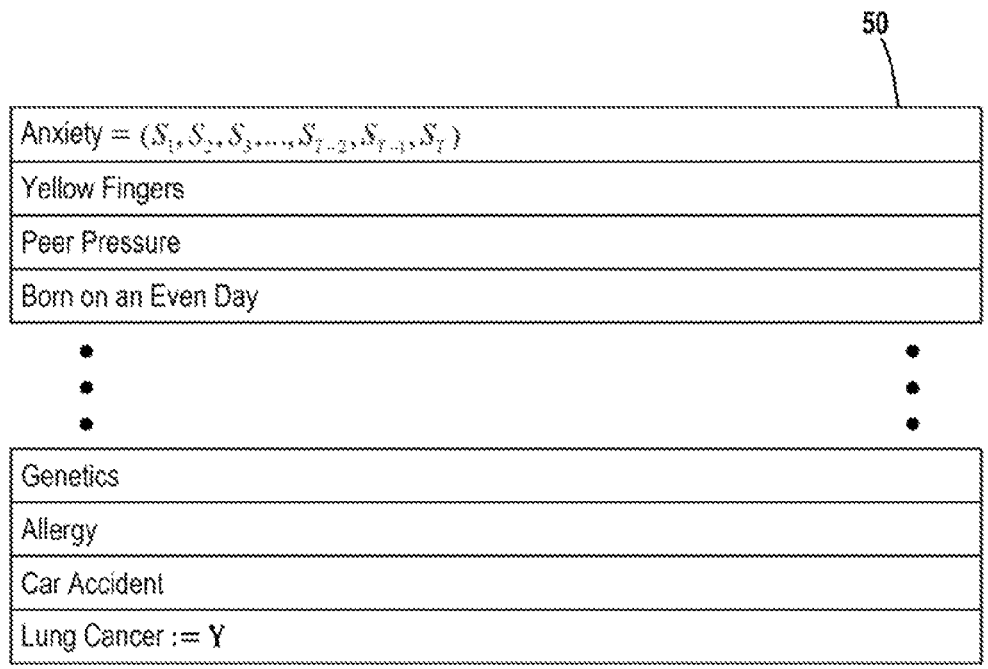
FIG. 11 schematically illustrates a multivariate feature dataset for feature relational analysis using the lsXGC method.

FIG. 11 illustrates a feature dataset 50 that defines a complete system $N_c$ containing N features related to lung cancer and containing T sets of simultaneous values for those features obtained from a sample population. It is desired to evaluate the relative relevancy of each feature as a source S on the target Y of the feature "lung cancer" (presence or absence of lung cancer) to evaluate the relative relevancy or importance of each of the other features on the presence or absence of lung cancer.

An analysis using a lsNGC variant of the lsXGC method was conducted using the lung cancer feature as the target Y and each of the other features as a source S to obtain a vector of relevancy indices to identify relevant factors for lung cancer.

The lsNGC method was used in essentially the same manner as used with multivariate time-series datasets to determine causality indices such as Granger causality indices or f-statistic indices. The lung cancer feature was predicted using dimension-reduced and augmented dimension-reduced representations as described above for multivariate time-series analysis. One machine learning model predicts the lung cancer feature utilizing the information from all of the other features except for the source S, and the other machine learning model predicts the lung cancer feature utilizing the information from all of the other features including the source S. Because the feature values are not sequential (time-ordered) data, all the appropriate data and not merely a windowed portion of the data were used for generating predictions.

The lsNGC method was able to successfully assign a high relevancy score to the five known relevant features of the data set even at small sample sizes. Results of the lsNGC method for feature selection appear very promising, but as always, the data analyst must investigate practical limitations of any method, the sufficiency of data, and other considerations when selecting and using any feature selection approach.

Figure 12:
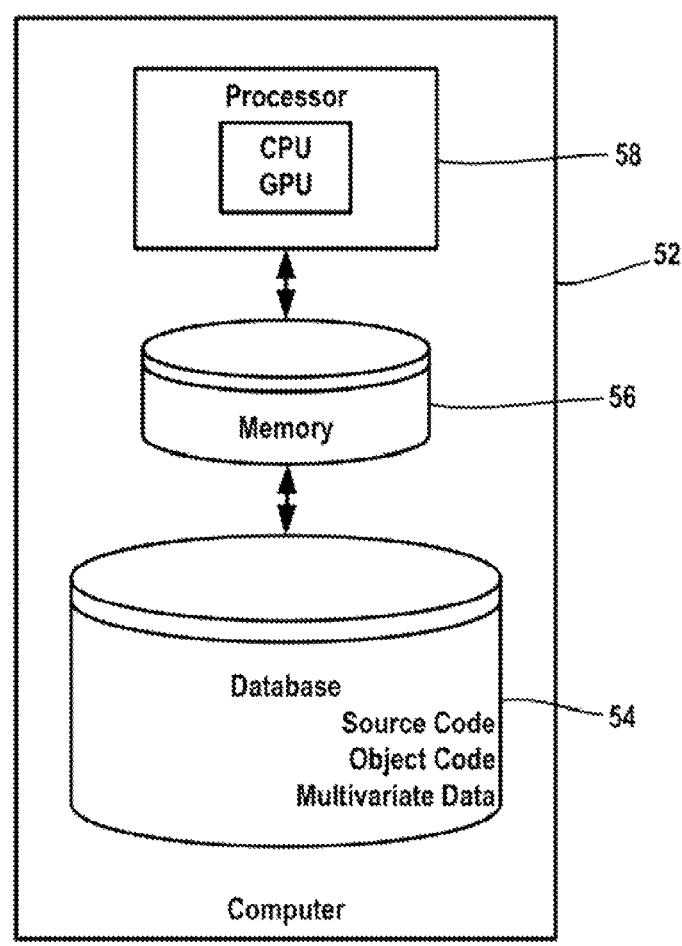
FIG. 12 schematically illustrates a computer implementation of the lsXGC method.

The lsXGC method, including its lsNGC variants, such as used for time-series causality analysis or feature relevance detection or feature selection, is a computer-implemented method, as it is not practical for hand-calculation. FIG. 12 is a schematic representation of a computer implementation for implementation of the lsXGC method. The computer implementation includes a computer 52 having a database 54, a memory 56, and a processor 58. The database stores computer instructions for carrying out the lsXGC method and the multivariate data for analysis using the lsXGC method. The computer instructions may be in a tangible, non-transient, processor-usable object code format and/or source code format of a programming language (such as Python, C, C++, C #, Java, JavaScript, Ruby, R, MATLAB, or the like) for translation or compilation into processor-usable object code. The processor reads the computer instructions from the database through a memory, and can write data such as an affinity matrix to the database through the memory. The processor may include one or more central processing units (CPUs), each CPU having one core or multiple cores. The processor may include one or more graphical processing units (GPUs) designed for efficient arithmetic processing of the algorithms and data structures often used in machine learning. The components of the computer may be wholly contained in a computer case, be distributed in a local area network, or distributed in a wide area network or cloud. For example, some cloud providers offer internet access to GPUs for use with machine learning applications. The method can also be partly or fully implemented by using quantum computers.

In a classic linear Granger causality application setting, multivariate autoregressive (MVAR) time-series estimation can be used, where the augmentation of dimension-reduced time-series systems by additional time-series, which contain information about the conditional source and/or target time-series, can be easily accomplished by adding extra dimensions for these additional time-series in the MVAR modeling approach. This is distinctly different from the large-scale Granger causality (lsGC) approach mentioned above. Note that the affine modeling approach explained previously can be seen as a one-dimensional version of an MVAR model.

Note that, although the lsXGC method so far has been mainly described for embodiments related to time-series analysis, the method can easily be generalized to other contexts. Instead of interpreting the rows and columns of the data matrices of a complete series $N_c$ as time-series (rows) and temporal samples (columns), or the rows as features and the columns as multi-dimensional data samples, i.e. as vectors, whose elements represent the value of each feature for a given sample. Instead of estimating the value of a target time-series at given points in time (e.g., future, past, present), the target may represent any quantity that may be estimated from the data samples. Thus, the described lsXGC method can be used to calculate measures that can serve as statistical surrogates of the "causal influence" of each feature on any chosen target quantity. The resulting measures can be used to determine the "relevance" of each feature for estimating the target, which can be used for feature selection in function approximation or supervised machine learning tasks. This is specifically important in high-dimensional settings, where the number of features is high, but the number of available data samples is low. Note that for lsXGC, inherent assumptions made for Granger causality, such as on the direction of causality, are not required, as discussed below.

The lsXGC method disclosed herein has been inspired by Granger causality, namely as a method for calculating a measure of causal influence of the conditional source on the target. It is very important to note that the lsXGC method is not limited to assumptions underlying any type of Granger causality. Such assumptions include, but are not limited to the following:

(1) Direction of time: Granger causality is usually based on an assumed direction of time: most often, the future of the target time-series is estimated from the present or past of the (complete) time-series system. Alternatively, time-reversed Granger causality methods have been described as well, e.g. [4]. Note that for the lsXGC method described herein, any subset of the target time-series may be estimated from any subset of time-points of any subset of time-series of the complete time-series system. Specifically, past, present, or future values of any time-series may be used for estimating the target.

(2) Direction of causality: Granger causality is typically used to calculate a measure of causal influence of the conditional source time-series on the target time-series. This implied direction of causality, i.e., from source to target, is not required for the lsXGC or its non-linear lsNGC variants. Specifically, lsXGC can be used for calculating a measure of causal influence of the target on the source, by using the computational steps explained herein. This does not mean simply re-naming source and target and repeating calculations with such exchanged roles. It means an actual inversion of the direction of inferred causality. At first glance, this may seem counter-intuitive, but is inspired by prior work on non-linear time-series analysis, e.g. [5]. Here, it is widely accepted that in many non-linear time-series systems, a causal driver may be estimated well from the causally driving time-series, but not vice-versa. In general, the computational steps of the lsXGC (lsNGC) method may be used to calculate measures of causal influence or any form of interdependence, such as motivated by appropriate information-theoretic measures, such as transfer entropy [6] or conditional mutual information [7], regardless whether such measures of causal influence or interdependence be unidirectional or bi-directional.

(3) Direct inference of causality: Note that the disclosed method can be used independently from methods that compare quantities calculated in the presence and the absence of information about the source dataset, such as Granger causality, transfer entropy, or conditional mutual information. Instead, measures of causal interdependence between source and target dataset can be directly calculated, even in a multivariate setting, such as the estimation errors obtained when calculating estimates of the target using linear or non-linear modeling approaches. For example, one can use one or more of the augmented dimensionally modified representations calculated in the lsXGC method for estimating values of the target using any linear or non-linear multivariate modeling method, and use the obtained estimation errors as measures of causal interdependence directly, e.g. in a multivariate, e.g. sliding-window based, estimation approach. This is inspired by above cited methods for non-linear time-series modeling e.g. [5], and can be also seen as a multivariate extension of Mutual Connectivity Analysis (MCA) based on the disclosed invention. Here, a specific embodiment could also include (i) selecting a target dataset; (ii) augmenting a dimensionally modified representation of a complete system, which contains information about more than one possible source dataset, with information about one specifically chosen source dataset, and calculating estimation errors for estimating the target dataset as a direct measure of causal interdependence between source and target dataset; (iii) iterating step (ii) for a different choice of source dataset; and (iv) comparing such obtained causal interdependence measures. Note that such an approach is also applicable to features datasets.

Given the aspects (1), (2), and (3) discussed in the preceding paragraph, the lsXGC (lsNGC) method draws a connection between Granger causality and certain traits of non-linear time-series analysis.

For the above described generalization of the lsXGC method to features, inverting the direction of causality would mean to interpret the target as features, the relevance of which for the conditional source can be evaluated by using the computational steps described herein. The above comments on calculating measures of causal influence or any form of interdependence between source and target hold as well for feature selection.

A "Divide and Conquer (D&C) strategy" for enhancing the computational efficiency in lsNGC is discussed next. Using the disclosed method, we can compute quantitative estimates for the presence of multivariate directed causal interaction for all $N^2$ directed connections between N network nodes and store these in a $N^2$ affinity matrix D. However, it still remains a significant challenge to implement this approach in practical situations, such as in functional MRI. Here, a major difficulty arises from the large number of time-series ($N\sim10^3$–$10^5$) for analyzing effective connectivity on a fine-grained brain atlas parcellation template or even on a state-of-the-art neuro-imaging voxel resolution scale with whole-brain coverage.

Instead of analyzing a small number, say $N\sim10^2$, of pre-selected brain regions of interest, such as in contemporary seed-based approaches to resting-state fMRI analysis, this leads to very large affinity matrices D with up to $N\sim10^{10}$ elements. Thus, for lsNGC, we will have to train up to $10^{10}$ models, e.g. supervised learning machines, as non-linear time-series estimators, e.g. $10^{10}$ neural networks, in order to compute all matrix elements of D. Even though high-performance computing equipment may be available to many widely, a 'brute force' approach to accomplish this goal still appears challenging. Here, a key observation is that the proposed lsNGC approach allows us to pursue an algorithmic 'Divide and Conquer' (D&C) strategy to successfully address the afore mentioned computational challenge.

Figure 13:
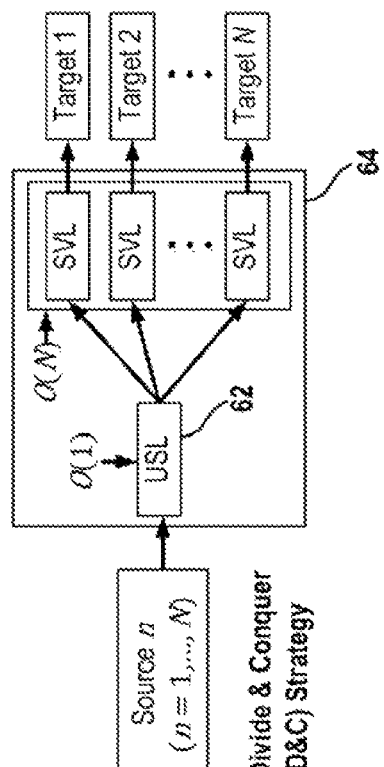
FIG. 13 schematically illustrates a "Divide and Conquer (D&C) strategy" for enhancing the computational efficiency of the lsNGC variant embodiment of the lsXGC method.
Figure 13:
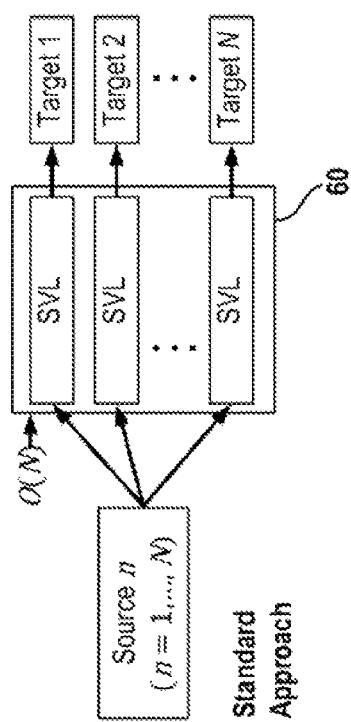

The D&C strategy is illustrated in FIG. 13. Instead of training N supervised learning (SVL) machines 60 for each source dataset directly, the D&C strategy disentangles the learning problem into one computationally expensive unsupervised learning (USL) step 62 and N subsequent computationally inexpensive SVL steps 64. In the lsNGC setting, each input source 66 corresponds to extracted multidimensional time-series windows resulting from a specific choice for the conditional source time-series S. As there are N such possible choices for S, the algorithmic complexity of calculating all $N^2$ elements of the affinity matrix, i.e. all lsNGC indices, is $O(N^2)$. By decoupling USL and SVL steps when choosing RBF (or GRBF) neural networks for the lsNGC, as explained above, we can decrease the empirical complexity dramatically, namely from $O(N^2)$ to almost $O(N)$, because the SVL step in (G)RBF networks is a computationally inexpensive matrix inversion. For a large number N of time-series as in fMRI analysis, the resulting increase of computational efficiency is substantial.

The D&C strategy can be directly adopted for lsNGC scheme, if we exploit the specific properties of (G)RBF neural networks. These can be interpreted as supervised learning machines, which are partially trained in an unsupervised way. In the (G)RBF network, non-linear feature extraction requires a vector quantization step to determine cluster centers and a subsequent computation of corresponding hidden-layer neuron activities, both of which do not depend on information about the prediction target, i.e., the desired network output. These steps constitute the computationally most expensive components in (G)RBF neural network training. However, these steps need to be performed only once for each input, regardless of how many different output prediction targets should be approximated by the network. Although the subsequent training of the (G)RBF network output weights needs to be performed in a supervised manner for each output, the corresponding computational expense is low, because this only implies a linear regression matrix inversion. I.e., one (G)RBF neural network needs to be trained for each conditional source S, which amounts to N such networks, where each (G)RBF network acts as a non-linear estimator for all N possible target time-series Y in the N-dimensional system.

Note that instead of using (G)RBF networks, we can similarly apply local models and multivariate regression techniques to apply the proposed D&C strategy. For example, when using such methods, defining a local neighborhood of a given data input, e.g. by k-nearest neighbor search, would correspond to the "unsupervised" learning step in FIG. 13, as a computationally expensive step, which, however, has to be performed only once for that source S (complexity O(N)), whereas calculating the local model or regression output for a single source/target pair (corresponding to the "supervised" learning step in FIG. 13) is computationally cheap, but has to be performed for all pairs of inputs and outputs in the system (complexity $O(N^2)$). In summary, by following the D&C strategy outlined in FIG. 13, i.e., by disentangling unsupervised and supervised learning steps when choosing RBF neural networks, local models, or multivariate regression techniques as non-linear estimation models for lsNGC, we will be able to decrease the empirical complexity of the affinity matrix computation dramatically, namely from $O(N^2)$ to almost $O(N)$ by decoupling the estimation procedure into an initial, computationally expensive step of complexity O(N), followed by a computationally inexpensive step of complexity $O(N^2)$. Note that the D&C approach can be applied to both time-series and features datasets.

Further analysis of causal interdependence measures calculated by the disclosed lsXGC (lsNGC) method can be performed in manifold ways. Specifically, such measures can be used as inputs for subsequent modeling, e.g. machine learning tasks, either directly or indirectly, e.g. after extraction of graph-theoretic network features, for classification or regression. For example, in network analysis applications, such as fMRI brain connectivity described above, the calculated causal interdependence measures between specific brain regions, or even whole $N^2$ connectivity matrices, may be used for classifying imaged human subjects as suffering from a certain neurologic condition or even estimate their clinical performance levels in neurocognitive tasks based on such fMRI analysis. Interestingly, the lsXGC method can also be applied for estimating the "relevance" of input features for such classification/regression tasks, e.g. for feature selection. Also, one can perform community detection in network graphs calculated from lsXGC (lsNGC)-derived connectivity matrices, such as by using graph-theoretic methods, the Louvain method, or non-metric clustering. For such network analysis and network-based inference applications, geometric deep learning methods, such as graph convolution networks (GCN) can be used.

The disclosed method may include the steps (a) and (b) of:
(a) calculating at least one of the following dimensionally modified representations (aa) and (ab):
  (aa) a dimensionally modified representation $n_i$ of one of the following three datasets (1), (2), and (3): (1) the confounding dataset B, (2) the target data set Y, and (3) the union of the confounding dataset B and the target dataset Y, whereby the representation $n_i$ does not include information about the source dataset S, and
  (ab) a dimensionally modified representation $n_c$ of at least one of the following datasets (1), (2), (3), and (4): (1) the source dataset S, (2) the union of the source dataset S and the confounding dataset B, (3) the union of the source dataset S and the target dataset Y, and (4) the union of the source dataset S, the confounding dataset B, and the target dataset Y; and
(b) constructing at least one of the following augmented dimensionally modified representations $m_i$ or $m_c$ by:
  (ba) constructing an augmented dimensionally modified representation $m_i$ that does not contain information about the source dataset S by augmenting a dimensionally modified representation $n_i$ with information about at least one of the following datasets (1), (2), and (3): (1) the target dataset Y, (2) the confounding dataset B, and (3) the union of the target dataset Y and the confounding dataset B; and/or
  (bb) constructing an augmented dimensionally modified representation $m_c$ that contains information about the source dataset S by:
    (bba) augmenting the dimensionally modified representation $n_c$ with information about at least one of the following datasets (1), (2), (3), and (4): (1) the source dataset S, (2) the confounding dataset B, (3) the target dataset Y, and (4) any union of at least two of the datasets S, B, and Y; or
    (bbb) augmenting the dimensionally modified representation $n_i$ or the augmented dimensionally modified representation $m_i$ with information about the source dataset S.; and A calculation of a dimensionally modified representation carried out as part of step (a) and/or step (b) immediately above may include performing: principal components analysis (PCA); single value decomposition (SVD); independent component analysis (ICA); clustering methods; kernel transformation; dimensionality reduction by autoencoders or their variants, e.g. variational autoencoders; divergence-based methods, such as stochastic neighbor embedding (SNE); exploratory observation machines (XOM); self-organizing maps (SOM); or any linear or non-linear dimensionality reduction method.

In practicing the disclosed method, estimates of any non-empty subset or any union of any of the following data sets may be calculated: target Y, source S, confounding data set B, dimensionally modified representations $n_j$, $n_c$, $m_j$, or $m_c$; and such calculations are performed using (i) linear methods, including, affine, autoregressive, such as MVAR, or any other linear regression methods; or (ii) non-linear methods, including, non-linear regression methods, feedforward multi-layer perceptrons, e.g. trained by error-back-propagation, radial basis functions (RBF) neural networks or generalized radial basis functions (GRBF) neural networks, support vector regression, fuzzy logic, random forests, decision trees, recurrent neural networks, including, but not limited to Echo State Networks or LSTMs; or (iii) any type of local models, including, local linear models or local average models; (iv) any type of ordinary or partial differential equation solvers; or (v) any combination of different modeling approaches, including, combining approaches previously recited herein, committee machines, boosting, bootstrap aggregating, mixture-of-experts, and/or ensemble learning or ensemble methods. At least one of the following may hold: (i) the used modeling approaches are IIV invariant, or (ii) a divide and conquer strategy is used, including, the use of radial basis functions or generalized radial basis functions neural networks, local models, or multidimensional regression techniques, or (iii) calculated measures of causal interdependence are used for network analysis, such as by using graph convolutional networks (GCN), calculation of graph-theoretic features, or community detection, such as by using non-metric clustering or Louvain method, or (iv) calculated measures of causal interdependence, or quantities derived thereof, are used as input to subsequent pattern recognition, such as classification or regression, tasks, including any supervised or unsupervised machine learning methods, such as GCN. Estimates of any non-empty subset or any union of any of the following data sets may be calculated: target Y, source S, confounding data set B, dimensionally modified representations $n_j$, $n_c$, $m_j$, or $m_c$; and such estimates are used for calculating quantities that characterize the target Y. The calculation of quantities that characterize the target Y may be based on inverting dimensional modification methods, such as inverting dimensionality reduction methods, including, inverse PCA, inverse SVD, or trained auto-encoders for dimensionality reduction.

In practicing the disclosed method, quantities may be calculated that statistically characterize the target Y, such as ensembles of estimates, frequency distributions, such as represented by histograms, estimates of probability distributions and/or their parameters, including, any type of statistical or information-theoretic measures between conditional source and target, such as transfer entropy or conditional mutual information.

In practicing the disclosed method, the time-series or feature datasets may be obtained by performing functional MRI; or pertain to science, technology, medicine, functional MRI, EEG, EKG, EEG, PET, CT, analysis of any multidimensional recordings in medicine, physiology or systems biology, econometrics, such as stock market or portfolio analysis, video analysis, robotics, seismology, astronomy, network connectivity analysis, including networks related to biological systems, communications, including web traffic or social media, or energy grids.

In practicing the disclosed method, method steps may be stored as tangible computer code and operable by a computer processor for computer implementation of the method.

While this disclosure includes one or more illustrative embodiments described in detail, it is understood that the one or more embodiments are each capable of modification and that the scope of this disclosure is not limited to the precise details set forth herein but include such modifications that would be obvious to a person of ordinary skill in the relevant art including (but not limited to) changes in supervised and unsupervised machine learning algorithms, dimensional modification algorithms, measures of causality, computer hardware and software for computer implementation, environment or field of use, ordering of method steps, and the like, as well as such changes and alterations that fall within the purview of the following claims.

REFERENCES

[1] Axel Wismüller et al., *Pair-wise Clustering of Large Scale Granger Causality Index Matrices for Revealing Communities*. Proc. of SPIE, Int. Soc. Opt. Eng. 2014 Mar. 13; 9038: doi:10.1117/12.2044340 (2014)

[2] Adora M. DSouza, Anas Z. Abidin, Lutz Leistritz, and Axel Wismüller: *Exploring connectivity with large-scale Granger causality on resting-state functional MRI*. Journal of Neuroscience Methods 287:68-79 (2017)

[3] John A. Lee, Michel Verleysen, *Nonlinear Dimensionality Reduction*, Springer, 2007.

[4] Irene Winkler, Danny Panknin, Daniel Bartz, Klaus-Robert Müller and Stefan Haufe: *Validity of time reversal for testing Granger causality*. arXiv:1509.07636v2 [math.ST]11 Feb. 2016

[5] G. Sugihara, R. May, H. Ye, C. H. Hsieh, E. R. Deyle, M. Fogarty, and S. Munch: *Detecting causality in complex ecosystems*. Science 338:496-500, 2012

[6] Schreiber T: *Measuring information transfer*. Phys Rev Lett 85(2):461-464 (2000)

[7] M. Palus, V. Komarek, Z. Hrncir, and K. Sterbova, Phys. Rev. E 63, 046211 (2001)

[8] Granger C., *Investigating causal relations by econometric models and cross-spectral methods*. Econometrica 37:424-38 (1969)

[9] Marinazzo D, et al., *Nonlinear parametric model for Granger analysis of time series*, Phys. Rev. E 73 066216 (2006)

[10] Ancona N, Stramaglia S, *An invariance property of predictors in kernel induced hypothesis spaces*. Neural Computation, volume 18, no. 4 (2006)

[11] Guyon et al. *Causal feature selection*. Technical report, Berkeley, Calif., March 2007

[12] Nadaraja E., *On estimating regression*. Theory Probabil Appl 9(1):141-142 (1964)

The invention claimed is:

1. A computer-implemented method for determining a measure of the causal interdependence of elements of a multivariate features dataset or of a multivariate time-series dataset, the dataset including a source dataset S and a target dataset Y in the simultaneous presence of a non-empty confounding dataset B, the confounding dataset B not being the source dataset S and not being the target dataset Y, the method being performed by computer and comprising the steps of:
- (a) calculating at least one of the following dimensionally modified representations (aa) and (ab):
  - (aa) a dimensionally modified representation $n_i$ of one of the following three datasets (1), (2), and (3): (1) the confounding dataset B, (2) the target data set Y, and (3) the union of the confounding dataset B and the target dataset Y, whereby the representation $n_i$ does not include information about the source dataset S, and
  - (ab) a dimensionally modified representation $n_c$ of at least one of the following datasets (1), (2), (3), and (4): (1) the source dataset S, (2) the union of the source dataset S and the confounding dataset B, (3) the union of the source dataset S and the target dataset Y, and (4) the union of the source dataset S, the confounding dataset B, and the target dataset Y;
- (b) constructing at least one of the following augmented dimensionally modified representations $m_i$ or $m_c$ by:
  - (ba) constructing an augmented dimensionally modified representation $m_i$ that does not contain information about the source dataset S by augmenting a dimensionally modified representation $n_i$ with information about at least one of the following datasets (1), (2), and (3): (1) the target dataset Y, (2) the confounding dataset B, and (3) the union of the target dataset Y and the confounding dataset B; and/or
  - (bb) constructing an augmented dimensionally modified representation $m_c$ that contains information about the source dataset S by:
    - (bba) augmenting the dimensionally modified representation $n_c$ with information about at least one of the following datasets (1), (2), (3), and (4): (1) the source dataset S, (2) the confounding dataset B, (3) the target dataset Y, and (4) any union of at least two of the datasets S, B, and Y; or
    - (bbb) augmenting the dimensionally modified representation $n_i$ or the augmented dimensionally modified representation $m_i$ with information about the source dataset S; and
- (c) calculating a measure of causal interdependence of the source dataset S and the target dataset Y using at least one of the augmented dimensionally modified representations $m_i$ or $m_c$, whereby information about the confounding data set B is used:
  - (1) directly, or
  - (2) indirectly by having the information about the confounding data set B having been included in the representations $n_i$, $n_c$, $m_i$, or $m_c$, which are used for calculating a measure of causal interdependence of the source dataset S and the target dataset Y.

2. The method of claim 1, wherein step (c) comprises:
calculating estimation errors that compare estimated and actual values of the target dataset Y, or
calculating information-theoretic quantities that characterize information exchange between the source dataset S and the target dataset Y.

3. The method of claim 1, wherein the calculation of a dimensionally modified representation $n_i$ is based on performing the calculation of a dimensionally modified representation $n_c$ in such a way that information about the source dataset S is eliminated.

4. The method of claim 1 wherein the calculation of the dimensionally modified representations $n_i$ or $n_c$ is performed in such a way that information about the target dataset Y or the confounding dataset B, or both, is eliminated from $n_i$ or $n_c$.

5. The method of claim 1 wherein step (c) comprises:
calculating quantities that provide information about the target dataset Y without using information about the source dataset S by basing the calculations of $\tilde{y}$:
- (i) on the dimensionally modified representation or
- (ii) on the augmented dimensionally modified representation $m_i$; and calculating quantities $\hat{y}$ that provide information about the target dataset Y using information about the source dataset S by basing the calculations of $\hat{y}$:
- (iii) on the dimensionally modified representation $n_c$, or
- (iv) on the augmented dimensionally modified representation $m_c$;

and the calculation of a measure of causal interdependence of the source dataset S and the target dataset Y is based on both quantities $\tilde{y}$ and $\hat{y}$.

6. The method of claim 5 wherein quantities $\tilde{y}$ and $\hat{y}$ are estimated values of the target dataset Y, whereby the calculation of a measure of causal interdependence of the source dataset S and the target dataset Y is based on the calculation of quantities that compare estimation errors of the estimated values $\tilde{y}$ and the estimated values $\hat{y}$ in estimating the target dataset Y.

7. The method of claim 5 wherein the quantities $\tilde{y}$ and $\hat{y}$ provide statistical information about the target dataset Y that is used to calculate information-theoretic measures that characterize information exchange between the source dataset S and the target dataset Y.

8. The method of claim 5, wherein calculating a measure of causal interdependence between the source dataset X and the target dataset Y comprises:
calculating Granger causality by calculating Granger causality indices or f-statistic.

9. The method of claim 1 wherein:
a complete dataset $N_c$ is defined as:
- the union of the source dataset S and the confounding dataset B, or
- the union of the source dataset S and the target dataset Y, or
- the union of the source dataset S, the confounding dataset B, and the target dataset Y; and step (a) comprises the steps of:
removing the source dataset S from the complete dataset $N_c$ to form the incomplete dataset $N_i$; and
calculating a dimensionally modified representation of $N_i$ to form $n_i$.

10. The method of claim 9 comprising the steps of:
iterating over a non-empty and at least two-element subset P of the complete dataset $N_c$, and for each iteration:
assigning one or more different non-empty subsets of P as the source dataset S;
removing that source dataset S from the complete dataset $N_c$ to form an incomplete dataset $N_i$ that includes the confounding dataset B; and
calculating the measure of causal interdependence of the source dataset S and a target dataset Y by performing steps (a)-(c), wherein step (a) comprises calculating the dimensionally modified representation $n_i$ from the incomplete dataset $N_i$.

11. The method of claim 9 comprising the steps of:
iterating over a non-empty and at least two-element subset Q of the complete dataset $N_c$, and for each iteration:

assigning one or more different non-empty subsets of Q as the target dataset Y; and calculating a measure of causal interdependence of the source dataset S and the target dataset Y by performing steps(a)-(c).

12. The method of claim 9 wherein one dimensionally modified representation $n_c$ of the complete dataset $N_c$ is calculated and used for more than one iteration by, in each iteration:

eliminating information about the source dataset S from $n_c$; and/or eliminating information about the target dataset Y from $n_c$.

13. The method of claim 1 wherein estimates of any non-empty subset or any union of any of the following data sets are calculated: target Y, source S, confounding data set B, dimensionally modified representations $n_i$, $n_c$, $m_i$, or $m_c$;

and such calculations are performed using (i) linear methods; or (ii) non-linear methods; or (iii) any type of local models, including, local linear models or local average models; or (iv) any type of ordinary or partial differential equation solvers; or (v) any combination of different modeling approaches, including, committee machines, boosting, bootstrap aggregating, mixture-of-experts, and/or ensemble learning or ensemble methods.

14. The method of claim 1 wherein the calculation of a dimensionally modified representation of the source dataset S, the target dataset Y, or the confounding data set B includes a non-linear transformation; and such a calculated dimensionally modified representation serves as input to linear modeling methods, including, affine or MVAR modeling.

15. The method of claim 1 wherein step (c) comprises:
calculating a measure of causal influence of a source dataset S on a target dataset Y; or,
calculating a measure of causal influence of a target data set Y on a source dataset S.

16. The method of claim 1 wherein the source dataset S, the target dataset Y, and the confounding dataset B are each time-series datasets.

17. The method of claim 1 wherein the source dataset S, the target dataset Y, and the confounding dataset B are each features datasets.

18. The method of claim 1 wherein the source dataset S, the target dataset Y, the confounding dataset B, or any union of at least two of these datasets, defines a dataset $X \in \mathbb{R}^{N \times T}$, wherein the dataset X is an underdetermined data set with $N > T$.

19. Computer code stored in a tangible medium and operable by a computer processor for computer implementation of the method as recited in claim 1.

20. A device for determining a measure of the causal interdependence of elements of a multivariate time-series dataset or of a multivariate features dataset, the device comprising:

one or more processors; and one or more memories storing code executable by the processors to perform:

(a) reading from the multivariate time-series dataset or from the multivariate features dataset a source dataset S, a target dataset Y, and a non-empty dataset B, the dataset B not being the source dataset S and not being the target dataset Y;

(b) calculating at least one of the following dimensionally modified representations (aa) and (ab):

(aa) a dimensionally modified representation $n_i$ of one of the following three datasets (1), (2), and (3): (1) a confounding dataset B, (2) a target data set Y, and (3) a union of the confounding dataset B and the target dataset Y, whereby the representation $n_i$ does not include information about the source dataset S, and (ab) a dimensionally modified representation $n_c$ of at least one of the following datasets (1), (2), (3), and (4): (1) the source dataset S, (2) the union of the source dataset S and the confounding dataset B, (3) the union of the source dataset S and the target dataset Y, and (4) the union of the source dataset S, the confounding dataset B, and the target dataset Y;

(c) constructing at least one of the following augmented dimensionally modified representations $m_i$ or $m_c$ by:

(ba) constructing an augmented dimensionally modified representation $m_i$ that does not contain information about the source dataset S by augmenting a dimensionally modified representation $n_i$ with information about at least one of the following datasets (1), (2), and (3): (1) the target dataset Y, (2) the confounding dataset B, and (3) the union of the target dataset Y and the confounding dataset B; and/or (bb) constructing an augmented dimensionally modified representation $m_c$ that contains information about the source dataset S by:

(bba) augmenting the dimensionally modified representation $n_c$ with information about at least one of the following datasets (1), (2), (3), and (4): (1) the source dataset S, (2) the confounding dataset B, (3) the target dataset Y, and (4) any union of at least two of the datasets S, B, and Y; or (bbb) augmenting the dimensionally modified representation $n_i$ or the augmented dimensionally modified representation $m_i$ with information about the source dataset S; and (d) calculating a measure of causal interdependence of the source dataset S and the target dataset Y using at least one of the augmented dimensionally modified representations $m_i$ or $m_c$, whereby information about the confounding data set B is used:

(1) directly, or (2) indirectly by having the information about the confounding data set B having been included in the representations $n_i$, $n_c$, $m_i$, or $m_c$, which are used for calculating a measure of causal interdependence of the source dataset S and the target dataset Y.

* * * * *

UNITED STATES PATENT AND TRADEMARK OFFICE
CERTIFICATE OF CORRECTION

PATENT NO. : 11,836,215 B2
APPLICATION NO. : 17/413273
DATED : December 5, 2023
INVENTOR(S) : Axel W. E. Wismüller Page 1 of 1

It is certified that error appears in the above-identified patent and that said Letters Patent is hereby corrected as shown below:

In the Claims

Column 26, Line 10, following "representation" insert -- $n_i$, --

Signed and Sealed this
Second Day of January, 2024

Katherine Kelly Vidal
*Director of the United States Patent and Trademark Office*